United States Patent
Koyanagi et al.

(10) Patent No.: US 10,629,818 B2
(45) Date of Patent: Apr. 21, 2020

(54) ORGANIC THIN-FILM TRANSISTOR AND METHOD FOR MANUFACTURING THE SAME, MATERIAL FOR ORGANIC THIN-FILM TRANSISTOR, COMPOSITION FOR ORGANIC THIN-FILM TRANSISTOR, COMPOUND, AND ORGANIC SEMICONDUCTOR FILM

(71) Applicants: FUJIFILM Corporation, Tokyo (JP); THE UNIVERSITY OF TOKYO, Tokyo (JP)

(72) Inventors: Masashi Koyanagi, Kanagawa (JP); Hiroaki Tsuyama, Kanagawa (JP); Eiji Fukuzaki, Kanagawa (JP); Yoshihisa Usami, Kanagawa (JP); Tetsuya Watanabe, Kanagawa (JP); Takashi Goto, Kanagawa (JP); Toshihiro Okamoto, Tokyo (JP); Junichi Takeya, Tokyo (JP)

(73) Assignees: FUJIFILM Corporation, Tokyo (JP); THE UNIVERSITY OF TOKYO, Tokyo (JP)

( * ) Notice: Subject to any disclaimer, the term of this patent is extended or adjusted under 35 U.S.C. 154(b) by 39 days.

(21) Appl. No.: 15/885,857

(22) Filed: Feb. 1, 2018

(65) Prior Publication Data

US 2018/0205021 A1    Jul. 19, 2018

Related U.S. Application Data

(63) Continuation of application No. PCT/JP2016/072629, filed on Aug. 2, 2016.

(30) Foreign Application Priority Data

Aug. 4, 2015 (JP) .................. 2015-154605
Aug. 1, 2016 (JP) .................. 2016-151064

(51) Int. Cl.
*H01L 51/00* (2006.01)
*H01B 1/00* (2006.01)
(Continued)

(52) U.S. Cl.
CPC ........ *H01L 51/0071* (2013.01); *C07D 345/00* (2013.01); *C07D 421/14* (2013.01);
(Continued)

(58) Field of Classification Search
CPC ..... H01B 1/12; H01L 29/786; H01L 51/0002; C07D 495/22; C07D 333/50; C07D 333/54; C07D 333/62
See application file for complete search history.

(56) References Cited

U.S. PATENT DOCUMENTS 9,960,364 B2 * 5/2018 Nakano ............... C07D 487/14
2010/0072887 A1 * 3/2010 Kwong ............... C07D 345/00
313/504
(Continued)

FOREIGN PATENT DOCUMENTS

JP    2012-503889 A    2/2012
JP    2013-197193 A    9/2013
(Continued)

OTHER PUBLICATIONS

Takeya et al "Aerobic oxidative dimerization of 1-naphthols to 2'2-binaphthoquinones . . . ", Tetrahedron 60 (2004) 9049-9060.*
(Continued)

*Primary Examiner* — Mark Kopec
(74) *Attorney, Agent, or Firm* — Studebaker & Brackett PC

(57) ABSTRACT

A compound which, when used for organic semiconductor films in organic thin-film transistors, makes the organic thin-film transistors exhibit a high carrier mobility, a mate-
(Continued)

rial for an organic thin-film transistor for which the compound is used, a composition for an organic thin-film transistor, an organic thin-film transistor and a method for manufacturing the same, and an organic semiconductor film. The organic thin-film transistor contains a compound represented by General Formula (1) in an organic semiconductor film (organic semiconductor layer) thereof.

General Formula (1)

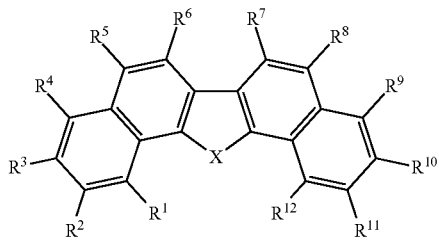

18 Claims, 3 Drawing Sheets

(51) Int. Cl.
C07D 345/00 (2006.01)
C07D 421/14 (2006.01)
C09B 57/00 (2006.01)
H01L 51/05 (2006.01)
H01L 29/786 (2006.01)
H01B 1/12 (2006.01)
C09D 5/24 (2006.01)

(52) U.S. Cl.
CPC ............. C09B 57/00 (2013.01); C09D 5/24 (2013.01); H01B 1/12 (2013.01); H01L 29/786 (2013.01); H01L 51/0068 (2013.01); H01L 51/05 (2013.01); H01L 51/0003 (2013.01); H01L 51/0004 (2013.01); H01L 51/0005 (2013.01); H01L 51/0545 (2013.01); H01L 51/0558 (2013.01)

(56) References Cited

U.S. PATENT DOCUMENTS

2013/0245282 A1 9/2013 Takeya et al.
2014/0034915 A1* 2/2014 Lee ................ H01L 51/0074
257/40
2015/0221876 A1 8/2015 Kitamura et al.
2016/0035984 A1 2/2016 Takaku et al.
2016/0322588 A1 11/2016 Koyanagi et al.

FOREIGN PATENT DOCUMENTS

JP 2014-168059 A 9/2014
JP 2015-048346 A 3/2015
JP 2015-109402 A 6/2015
WO 2014/061465 A1 4/2014
WO 2014/119712 A1 8/2014
WO 2015/046523 A1 4/2015
WO 2015/111605 A1 7/2015

OTHER PUBLICATIONS

An Office Action mailed by the Japanese Patent Office dated Feb. 12, 2019, which corresponds to Japanese Patent Application No. 2017-533081 and is related to U.S. Appl. No. 15/885,857.
Chikahiko Mitsui et al., Dinaphtho [1,2-b:2',1'-d] chalcogenophenes: Comprehensive Investigation of the Effect of the Chalcogen Atoms in the Phenacene-Type p Electronic Cores, Chemistry of Materials, Sep. 14, 2013, 25(20), pp. 3952-3956.
International Search Report issued in PCT/JP2016/072629; dated Oct. 25, 2016.
Written Opinion issued in PCT/JP2016/072629; dated Oct. 25, 2016.
The extended European search report issued by the European Patent Office dated Apr. 17, 2018, which corresponds to European Patent Application No. 16833030.6-1110 and is related to U.S. Appl. No. 15/885,857.
Alam Ashraful et al., "A new method for the synthesis of dinaphtho [1,2-b;2',1'-d] thiophenes and selenophenes", Heteroatom Chemistry, John Wiley & Sons, Inc., US, vol. 18, No. 3, Apr. 1, 2007, pp. 239-248, XP009504551, ISSN: 1042-7163, DOI: 10.1002/HC. 20291.
Cocker W et al., "The elimination of non-angular alkyl groups in aromatisation reactions", Journal of the Chemical Society, Chemical Society, Letchworth, GB, Jan. 1, 1953, pp. 2355-2362, XP002238332, ISSN: 0368-1769, DOI: 10.1039/JR9530002355.

* cited by examiner

ORGANIC THIN-FILM TRANSISTOR AND METHOD FOR MANUFACTURING THE SAME, MATERIAL FOR ORGANIC THIN-FILM TRANSISTOR, COMPOSITION FOR ORGANIC THIN-FILM TRANSISTOR, COMPOUND, AND ORGANIC SEMICONDUCTOR FILM

CROSS-REFERENCE TO RELATED APPLICATIONS

This application is a Continuation of PCT International Application No. PCT/JP2016/072629 filed on Aug. 2, 2016, which claims priority under 35 U.S.C. § 119(a) to Japanese Patent Application No. 2015-154605 filed on Aug. 4, 2015 and Japanese Patent Application No. 2016-151064 filed on Aug. 1, 2016. Each of the above applications is hereby expressly incorporated by reference, in its entirety, into the present application.

BACKGROUND OF THE INVENTION

1. Field of the Invention

The present invention relates to an organic thin-film transistor and a method for manufacturing the same, a material for an organic thin-film transistor, a composition for an organic thin-film transistor, a compound, an organic semiconductor film, and the like.

2. Description of the Related Art

Organic thin-film transistors (organic TFT) having organic semiconductor films (organic semiconductor layers) are used in field-effect transistors (FET) that are used in liquid crystal displays or organic electroluminescence (EL) displays, apparatuses in which logic circuits are used such as radio frequency identifier (RFID: RF tag) or memories, or the like since weight reduction, cost reduction, and softening are possible.

It is known that, as compounds for forming the above-described organic semiconductor films, polycondensed compounds including heteroaromatic rings are useful.

For example, JP2015-48346A discloses a dinaphthothiophene compound having a substituent such as a long-chain alkyl. In JP2015-48346A, it is described that, in a case in which the above-described constitution is provided, it is possible to favorably pack molecules in fine crystals in organic active layers that are formed using fine crystal thin films and obtain excellent transistor performance (carrier mobility).

Meanwhile, JP2014-168059A describes a compound which has a dibenzocarbazole skeleton and has specific substituents on an N atom of carbazole and a carbon atom constituting the ring of the dibenzocarbazole skeleton. In JP2014-168059A, it is described that, in a case in which the above-described constitution is provided, that is, the volume of the substituent on the N atom of the carbazole in the compound having a dibenzocarbozole skeleton is decreased so as to obtain the sufficient overlapping of the electron orbital with adjacent molecules and, furthermore, a specific substituent is introduced into the carbon atom constituting the ring of the dibenzocarbazole skeleton, organic transistors having an excellent carrier mobility can be obtained.

SUMMARY OF THE INVENTION

In recent years, from the viewpoint of improving the performance of organic thin-film transistors, there has been a current demand for the additional improvement of the carrier mobility of organic thin-film transistors.

In response to such a demand, the present inventors carried out additional studies regarding organic thin-film transistors for which a polycondensed compound having a dinaphtho skeleton as disclosed in JP2015-48346A and JP2014-168059A is used and found that there is a room for the additional improvement of the carrier mobility.

Therefore, an object of the present invention is to provide a compound which, when used for organic semiconductor films in organic thin-film transistors, makes the organic thin-film transistors exhibit a high carrier mobility, a material for an organic thin-film transistor for which the compound is used, a composition for an organic thin-film transistor, an organic thin-film transistor and a method for manufacturing the same, and an organic semiconductor film.

As a result of intensive studies regarding the above-described object, the present inventors found that the use of a compound represented by General Formula (1) enables the obtainment of desired effects and completed the present invention.

That is, the present inventors found that the object can be achieved by the following constitutions.

<1> An organic thin-film transistor comprising: an organic semiconductor film including a compound which is represented by General Formula (1) and has a molecular weight of 3,000 or less.

<2> The organic thin-film transistor according to <1>, in which, in General Formula (1), the number of carbon atoms included in each of $R^3$ and $R^{10}$ is independently 1 to 30.

<3> The organic thin-film transistor according to <1> or <2>, in which, in General Formula (1), $R^3$ and $R^{10}$ each independently have, as $R^W$, an alkyl group having 1 to 20 carbon atoms, an alkynyl group having 2 to 6 carbon atoms, an aryl group having 6 to 20 carbon atoms, and a heteroaryl group having 3 to 20 carbon atoms, all of which may have a substituent.

<4> The organic thin-film transistor according to any one of <1> to <3>, in which, in General Formula (1), $R^1$ and $R^{12}$ are the same group, $R^2$ and $R^{11}$ are the same group, $R^3$ and $R^{10}$ are the same group, $R^4$ and $R^9$ are the same group, $R^5$ and $R^8$ are the same group, and $R^6$ and $R^7$ are the same group.

<5> The organic thin-film transistor according to any one of <1> to <4>, in which X is a selenium atom.

<6> The organic thin-film transistor according to any one of <1> to <5>, in which the compound is represented by General Formula (2).

<7> The organic thin-film transistor according to <6>, in which, in General Formula (2), $L^W$ is a single bond.

<8> The organic thin-film transistor according to any one of <1> to <7>, in which $R^3$ and $R^{10}$ each independently include a linear alkyl group.

<9> A compound which is represented by General Formula (1) and has a molecular weight of 3,000 or less.

<10> The compound according to <9>, in which, in General Formula (1), the number of carbon atoms included in each of $R^3$ and $R^{10}$ is independently 1 to 30.

<11> The compound according to <9> or <10>, in which, in General Formula (1), $R^3$ and $R^{10}$ each independently have, as $R^W$, an alkyl group having 1 to 20 carbon atoms, an alkynyl group having 2 to 6 carbon atoms, an aryl group having 6 to 20 carbon atoms, and a heteroaryl group having 3 to 20 carbon atoms, all of which may have a substituent.

<12> The compound according to any one of <9> to <11>, in which, in General Formula (1), $R^1$ and $R^{12}$ are the same group. $R^2$ and $R^{11}$ are the same group, $R^3$ and $R^{10}$ are the same group, $R^4$ and $R^9$ are the same group, $R^5$ and $R^8$ are the same group, and $R^6$ and $R^7$ are the same group.

<13> The compound according to any one of <9> to <12>, in which X is a selenium atom.

<14> The compound according to any one of <9> to <13>, in which the compound is represented by General Formula (2).

<15> The compound according to <14>, in which, in General Formula (2), $L^W$ is a single bond.

<16> The compound according to any one of <9> to <15>, in which $R^3$ and $R^{10}$ each independently include a linear alkyl group.

<17> A material for an organic thin-film transistor comprising: the compound according to any one of <9> to <16>.

<18> A composition for an organic thin-film transistor comprising: the compound according to any one of <9> to <16>; and a solvent.

<19> A method for manufacturing an organic thin-film transistor comprising: a step of forming an organic semiconductor film by applying the composition for an organic thin-film transistor according to <18> on a substrate and drying the composition.

<20> An organic semiconductor film comprising: the compound according to any one of <9> to <16>.

In the present specification, the expression of a compound is used to refer to the compound, and, additionally, a salt thereof and an ion thereof.

In the present specification, in a case in which a plurality of substituents, linking groups, or the like (hereinafter, referred to as substituents or the like) is indicated by a specific reference sign or a plurality of substituents or the like is specified at the same time, the respective substituents or the like may be identical to or different from one another. This is also true in the case of specifying the number of substituents or the like.

In addition, unless particularly otherwise described, in a case in which a plurality of substituents or the like comes close to one another (particularly, is adjacent to one another), the substituents or the like may be linked or condensed to one another and thus form a ring.

Furthermore, in the present specification, substituents or the like that are not clarified as being substituted or nonsubstituted may further have a substituent therein unless intended effects are not impaired. This is also true for compounds that are not clarified as being substituted or nonsubstituted.

In the present specification, numerical ranges expressed using "to" include numerical values before and after "to" as the lower limit value and the upper limit value.

According to the present invention, it is possible to provide a compound which, when used for organic semiconductor films in organic thin-film transistors, makes the organic thin-film transistors exhibit a high carrier mobility, a material for an organic thin-film transistor for which the compound is used, a composition for an organic thin-film transistor, an organic thin-film transistor and a method for manufacturing the same, and an organic semiconductor film.

DESCRIPTION OF THE PREFERRED EMBODIMENTS

[Organic Thin-Film Transistor]

Figure 1:
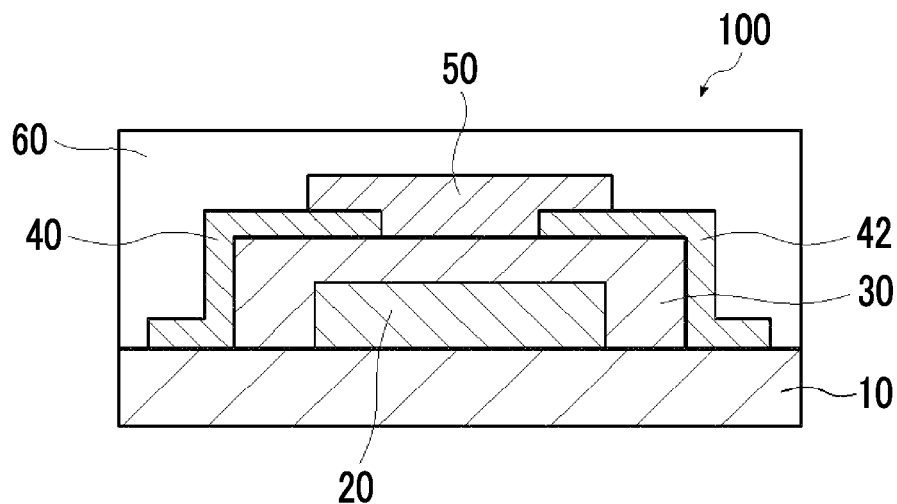
FIG. 1 is a schematic cross-sectional view of a bottom contact-type organic thin-film transistor according to an embodiment of the present invention.

An organic thin-film transistor of the present invention includes a compound which is represented by General Formula (1) and has a molecular weight of 3,000 or less in an organic semiconductor film (organic semiconductor layer) thereof.

The compound represented by General Formula (1) has a characteristic that, in organic semiconductor layers formed of fine crystal thin films, the phases of the electron orbitals of molecules in fine crystals favorably match, the interaction among the respective molecules is strong, and the molecules are excellently packed, and thus the highest occupied molecular orbitals (HOMO) of the molecules are likely to overlap one another.

That is, it is considered that, in a dinaphtho skeleton structure as represented by General Formula (1), in a case in which a chalcogen atom-containing hetero ring is included as a heteroaromatic ring in molecules, and furthermore, a selenium atom or a tellurium atom that has a larger molecular size than a sulfur atom is included, compared with dinaphthothiophene compounds or dibenzocarbazole skeleton compounds as described in JP2015-48346A and JP2014-168059A, the interaction between parent skeletons is stronger, and the HOMO orbitals of the molecules are more likely to overlap one another. As a result, the compound has a higher carrier mobility than the compound described in JP2015-48346A and JP2014-168059A.

<Compound Represented by General Formula (1)>

The compound represented by General Formula (1) is included in the organic semiconductor film (organic semiconductor layer) of the organic thin-film transistor.

The compound represented by General Formula (1) is a new compound and can not only be preferably used in the organic semiconductor film of the organic thin-film transistor but also be used in other uses described below.

General Formula (1)

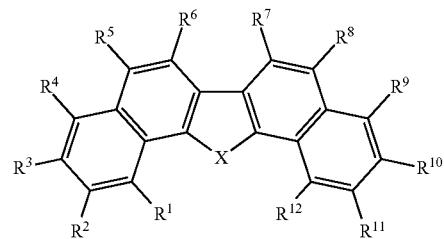

In General Formula (1), X represents an oxygen atom, a selenium atom, or a tellurium atom, and $R^1$ to $R^{12}$ each independently represent a group represented by Formula (W). Here, among $R^1$ to $R^{12}$, at least one group is a group other than a hydrogen atom.

$$-L^W-R^W \qquad (W)$$

In Formula (W), $L^W$ is a divalent linking group of any of a single bond, —O—, —S—, —NR$^{13}$—, —CO—, —SO—, —SO$_2$—, or —Si(R$^{14}$)(R$^{15}$)— or a divalent linking group obtained by bonding two or more divalent linking groups described above, and $R^W$ represents a hydrogen atom or an alkyl group, an alkenyl group, an alkynyl group, an aryl group, or a heteroaryl group, all of which may have a substituent.

$R^{13}$ to $R^{15}$ represent a hydrogen atom or an alkyl group, an alkenyl group, an alkynyl group, an aryl group, or a heteroaryl group, all of which may have a substituent.

Meanwhile, in the present specification, unless particularly otherwise described, "alkyl groups" and "alkenyl groups" refer to all of linear, branched, and cyclic alkyl groups and all of linear, branched, and cyclic alkenyl groups. Meanwhile, examples of cyclic alkyl groups include a cycloalkyl group, a bicycloalkyl group, a tricycloalkyl group, and the like. In addition, examples of cyclic alkenyl groups include a cycloalkenyl group, a bicycloalkenyl group, and the like.

In addition, in the present specification, example of hetero atoms included in "heteroaryl groups" include a sulfur atom (S), an oxygen atom (O), a nitrogen atom (N), and the like.

The molecular weight of the compound represented by General Formula (1) is 3,000 or less, preferably 250 to 2,000, more preferably 300 to 1,000, and still more preferably 350 to 800. The molecular weight is preferably set in the above-described range since it is possible to further increase the solubility in solvents.

In General Formula (1), X represents an oxygen atom, a selenium atom, or a tellurium atom, and, from the viewpoint of the large molecular size and the favorable overlapping of the HOMO orbitals, X is preferably a tellurium atom or a selenium atom and particularly preferably a selenium atom. Compared with a tellurium atom, a selenium atom has an appropriate molecular size, that is, in a case in which X is a selenium atom, compared with a case in which X is a tellurium atom, the orbital coefficient of a chalcogen atom improves without causing the crystal structure to be disordered (in other words, without causing deviation between parent skeletons), and thus the overlapping of the HOMO orbitals becomes more favorable.

In General Formula (1), $R^1$ to $R^{12}$ each independently represent a group represented by Formula (W).

$L^W$ is a divalent linking group of any of a single bond, —O—, —S—, —NR$^{13}$—, —CO—, —SO—, —SO$_2$—, or —Si(R$^{14}$)(R$^{15}$)— or a divalent linking group obtained by bonding two or more divalent linking groups described above, preferably a single bond, —O—, —S—, —NR$^{13}$—, —CO—, —O—CO—, —CO—O—, —NR$^{13}$—CO—, —CO—NR$^{13}$—, —O—CO—O—, —NR$^{13}$—CO—O—, —OCO—NR$^{13}$— or —NR$^{13}$—CO—NR$^{13}$—, more preferably a single bond, —O—, —S—, —NR$^{13}$—, —CO—, —O—CO—, or —CO—O—, and still more preferably a single bond.

$R^{13}$ to $R^{15}$ represent a hydrogen atom or an alkyl group (preferably having 1 to 20 carbon atoms), an alkenyl group (preferably having 2 to 6 carbon atoms), an alkynyl group (preferably having 2 to 6 carbon atoms), an aryl group (preferably having 6 to 14 carbon atoms), or a heteroaryl group (preferably having 3 to 12 carbon atoms), all of which may have a substituent and is preferably a hydrogen atom, an alkyl group, or an aryl group, more preferably a hydrogen atom or an alkyl group, and still more preferably an alkyl group having 1 to 8 carbon atoms.

$R^W$ represents a hydrogen atom, or an alkyl group, an alkenyl group, an alkynyl group, an aryl group, or a heteroaryl group, all of which may have a substituent.

The alkyl group is preferably an alkyl group having 1 to 20 carbon atoms, more preferably an alkyl group having 2 to 15 carbon atoms, and still more preferably an alkyl group having 3 to 10 carbon atoms. The alkyl group is preferably a linear alkyl group.

The alkenyl group is preferably an alkenyl group having 2 to 6 carbon atoms, more preferably an alkenyl group having 2 to 4 carbon atoms, and still more preferably an alkenyl group having 2 carbon atoms.

The alkynyl group is preferably an alkynyl group having 2 to 6 carbon atoms, more preferably an alkynyl group having 2 to 4 carbon atoms, and still more preferably an alkynyl group having 2 carbon atoms.

The aryl group is preferably an aryl group having 6 to 20 carbon atoms, more preferably an aryl group having 6 to 14 carbon atoms, and still more preferably an aryl group having 6 to 10 carbon atoms.

The heteroaryl group is preferably a heteroaryl group having 3 to 20 carbon atoms, more preferably a heteroaryl group having 3 to 12 carbon atoms, and still more preferably a heteroaryl group having 3 to 8 carbon atoms.

In General Formula (1), at least one of $R^1$, . . . , or $R^{12}$ is a group other than a hydrogen atom (hereinafter, referred to as "substituent W"). In $R^1$ to $R^{12}$ in General Formula (1), the number of the substituents W is preferably 2 to 4 and more preferably 2.

In the substituents W, from the viewpoint of the intermolecular interaction and the solubility, the number of carbon atoms is preferably 30 or less, more preferably 25 or less, still more preferably 20 or less, and particularly preferably 16 or less. In other words, the number of carbon atoms included in each of $R^1$ to $R^{12}$ (the total number of carbon atoms included in both $L^W$ and $R^W$ in Formula (W)) is preferably in the above-described numerical range independently.

In General Formula (1), in a case in which the substituents W are introduced into $R^1$ to $R^{12}$, the entire molecule preferably forms a line symmetric structure. That is, the substituents W are preferably introduced into locations in which the entire molecule forms a line symmetric structure so that the entire molecule, including the structure of $R^1$ to $R^{12}$, forms a line symmetric structure. Specifically, a case in which the substituents W (preferably substituents of the same kind) are present at the locations of both $R^1$ and $R^{12}$, a case in which the substituents W (preferably substituents of the same kind) are present at the locations of both $R^2$ and $R^{11}$, a case in which the substituents W (preferably substituents of the same kind) are present at the locations of both $R^3$ and $R^{10}$, a case in which the substituents W (preferably substituents of the same kind) are present at the locations of both $R^4$ and $R^9$, a case in which the substituents W (preferably substituents of the same kind) are present at the locations of both $R^5$ and $R^8$, a case in which the substituents W (preferably substituents of the same kind) are present at the locations of both $R^6$ and $R^7$, and combinations of two or more cases described above are preferred. Among these, from the viewpoint of the crystal structure and the intermolecular interaction, the case in which the substituents W are present at the locations of both $R^3$ and $R^{10}$ is more preferred.

In General Formula (1), from the viewpoint of the intermolecular interaction and the solubility, at least one of $R^1, \ldots,$ or $R^{12}$ preferably has, as $R^W$, an alkyl group having 1 to 20 carbon atoms, an alkynyl group having 2 to 6 carbon atoms, an aryl group having 6 to 20 carbon atoms, or a heteroaryl group having 3 to 20 carbon atoms, all of which may have a substituent, in at least one of the combinations of $R^1$ and $R^{12}$, $R^2$ and $R^{11}$, $R^3$ and $R^{10}$, $R^4$ and $R^9$, $R^5$ and $R^8$, or $R^6$ and $R^7$ each preferably have the above-described groups independently, and $R^3$ and $R^{10}$ each more preferably have the above-described groups independently. Meanwhile, the more preferred range of the alkyl group having 1 to 20 carbon atoms, the alkynyl group having 2 to 6 carbon atoms, the aryl group having 6 to 20 carbon atoms, or the heteroaryl group having 3 to 20 carbon atoms is as described above. Among these, in the alkyl group having 1 to 20 carbon atoms, the number of carbon atoms is preferably two or more.

In General Formula (1), from the viewpoint of the intermolecular interaction and the solubility, it is preferable that at least one of $R^1, \ldots,$ or $R^{12}$ each independently includes a linear alkyl group, and it is more preferable that at least one of the combinations of $R^1$ and $R^{12}$, $R^2$ and $R^{11}$, $R^4$ and $R^9$, $R^5$ and $R^8$, or $R^6$ and $R^7$ each independently include a linear alkyl group groups, and it is particularly preferable that the combinations of $R^3$ and $R^{10}$ each independently include a linear alkyl group. For example, in a case in which $R^3$ to $R^{10}$ have, as $R^W$, an alkyl group having 1 to 20 carbon atoms as described above, this alkyl group having 1 to 20 carbon atoms is preferably a linear alkyl, and, for example, in a case in which the groups have, as $R^W$, an aryl group having 6 to 20 carbon atoms, the aryl group preferably further has a linear alkyl group as a substituent. In summary, in other words, in a case in which $R^W$ is a group other than an alkyl group and represents an alkenyl group, an alkynyl group, an aryl group, or a heteroaryl group, the substituent in $R^W$ is preferably a linear alkyl group.

In General Formula (1), examples of the substituent that the alkyl group, the alkenyl group, the alkynyl group, the aryl group, and the heteroaryl group as $R^1$ to $R^{13}$ include a halogen atom, an alkyl group (including a cycloalkyl group, a bicycloalkyl group, and a tricycloalkyl group), an aryl group, a heterocyclic group (also referred to as "heterocyclic group"), a cyano group, a hydroxy group, a nitro group, a carboxy group, an alkoxy group, an aryloxy group, a silyl group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group (—B(OH)$_2$), a phosphate group (—OPO(OH)$_2$), a sulfate group (—OSO$_3$H), and other well-known substituents.

Among these, the substituent is preferably a halogen atom, an alkyl group (the alkyl group is preferably a linear alkyl group), an alkoxy group, an alkylsilyl group, or an aryl group, more preferably a fluorine atom, a substituted or unsubstituted alkyl group having 1 to 10 carbon atoms, a substituted or unsubstituted alkoxy group having 1 to 10 carbon atoms, a substituted or unsubstituted alkylsilyl group having 1 to 30 carbon atoms, or a phenyl group, still more preferably a fluorine atom, a substituted or unsubstituted alkyl group having 1 to 10 carbon atoms, a substituted or unsubstituted alkoxy group having 1 to 10 carbon atoms, or a substituted or unsubstituted alkylsilyl group having 1 to 30 carbon atoms, and particularly preferably a fluorine atom, a substituted or unsubstituted alkyl group having 1 to 10 carbon atoms, or a substituted or unsubstituted alkylsilyl group having 1 to 30 carbon atoms.

From the viewpoint of further improving the symmetry of the molecule and consequently improving the intermolecular interaction, it is preferable that $R^1$ and $R^{12}$ are the same group, $R^2$ and $R^{11}$ are the same group. $R^3$ and $R^{10}$ are the same group, $R^4$ and $R^9$ are the same group, $R^5$ and $R^8$ are the same group, and $R^6$ and $R^7$ are the same group.

The compound represented by General Formula (1) is preferably a compound which is represented by General Formula (2) and has a molecular weight of 3,000 or less.

General Formula (2)

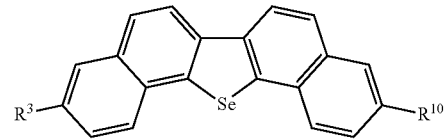

In General Formulae (2), $R^3$ to $R^{10}$ are the same group and each represent a group represented by Formula (W).

$$\text{-L}^W\text{-R}^W \qquad (W)$$

In Formula (W), $L^W$ is a divalent linking group of any of a single bond. —O—, —S—, —NR$^{13}$—, —CO—, —SO—, —SO$_2$—, or —Si(R$^{14}$)(R$^{15}$) or a divalent linking group obtained by bonding two or more divalent linking groups described above, and $R^W$ represents an alkyl group having 1 to 20 carbon atoms, an aryl group having 6 to 20 carbon atoms, or a heteroaryl group having 3 to 20 carbon atoms, all of which may have a substituent.

$R^{13}$ to $R^{15}$ each independently represent a hydrogen atom or an alkyl group, an alkenyl group, an alkynyl group, an aryl group, or a heteroaryl group, all of which may have a substituent.

Meanwhile, the preferred aspects of $R^3$ and $R^{10}$ in General Formula (2) are the same as those of $R^3$ and $R^{10}$ in General Formula (1).

Specific examples of the compound represented by General Formula (1) will be illustrated.

In the tables, "TMS" represents a trimethylsilyl group, "TIPS" represents triisopropylsilyl group, "Bu" represents a butyl group, "Et" represents an ethyl group, "Me" represents a methyl group, and "Ph" represents a phenyl group.

TABLE 1

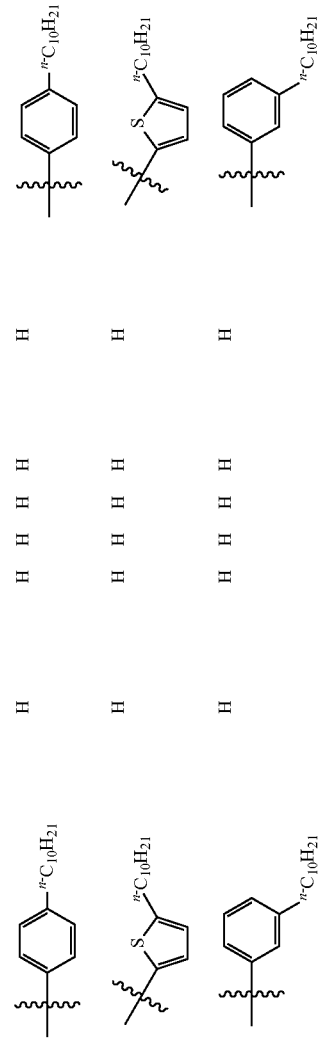

| Specific examples | R1 | R2 | R3 | R4 | R5 | R6 | R7 | R8 | R9 | R10 | R11 | R12 |
|---|---|---|---|---|---|---|---|---|---|---|---|---|
| 1 | H | H | n-$C_{10}H_{21}$ | H | H | H | H | H | H | n-$C_{10}H_{21}$ | H | H |
| 2 | H | H | n-$C_9H_{19}$ | H | H | H | H | H | H | n-$C_9H_{19}$ | H | H |
| 3 | H | H | n-$C_8H_{17}$ | H | H | H | H | H | H | n-$C_8H_{17}$ | H | H |
| 4 | H | H | n-$C_7H_{15}$ | H | H | H | H | H | H | n-$C_7H_{15}$ | H | H |
| 5 | H | H | n-$C_6H_{13}$ | H | H | H | H | H | H | n-$C_6H_{13}$ | H | H |
| 6 | H | H | n-$C_5H_{11}$ | H | H | H | H | H | H | n-$C_5H_{11}$ | H | H |
| 7 | H | H | n-$C_4H_9$ | H | H | H | H | H | H | n-$C_4H_9$ | H | H |
| 8 | H | H | n-$C_3H_7$ | H | H | H | H | H | H | n-$C_3H_7$ | H | H |
| 9 | H | H | n-$C_{11}H_{23}$ | H | H | H | H | H | H | n-$C_{11}H_{23}$ | H | H |
| 10 | H | H | n-$C_{12}H_{25}$ | H | H | H | H | H | H | n-$C_{12}H_{25}$ | H | H |
| 11 | H | H | Et | H | H | H | H | H | H | Et | H | H |
| 12 | H | H | Me | H | H | H | H | H | H | Me | H | H |
| 13 | H | H | 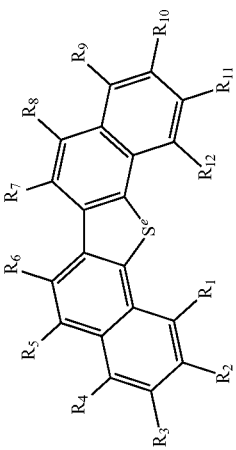 p-$C_{10}H_{21}$-phenyl | H | H | H | H | H | H | p-$C_{10}H_{21}$-phenyl | H | H |
| 14 | H | H | 5-n-$C_{10}H_{21}$-thienyl | H | H | H | H | H | H | 5-n-$C_{10}H_{21}$-thienyl | H | H |
| 15 | H | H | m-$C_{10}H_{21}$-phenyl | H | H | H | H | H | H | m-$C_{10}H_{21}$-phenyl | H | H |

TABLE 1-continued
STRUCTURAL FORMULA
| Specific examples | R1 | R2 | R3 | R4 | R5 | R6 | R7 | R8 | R9 | R10 | R11 | R12 |
|---|---|---|---|---|---|---|---|---|---|---|---|---|
| 16 | H | H | 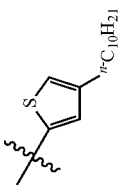 | H | H | H | H | H | H |  | H | H |
| 17 | H | H | 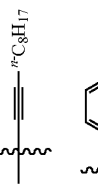 | H | H | H | H | H | H | 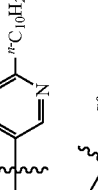 | H | H |
| 18 | H | H | t-Bu | H | H | H | H | H | H | t-Bu | H | H |
| 19 | H | H | TMS | H | H | H | H | H | H | TMS | H | H |
| 20 | H | H | 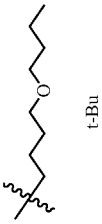 | H | H | H | H | H | H | 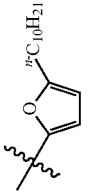 | H | H |
| 21 | H | H | 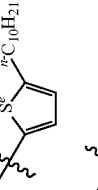 | H | H | H | H | H | H | 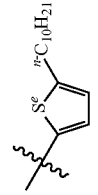 | H | H |
| 22 | H | H |  | H | H | H | H | H | H | 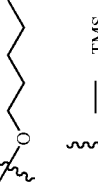 | H | H |
| 23 | H | H | 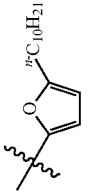 | H | H | H | H | H | H | 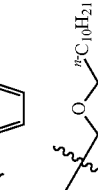 | H | H |
| 24 | H | H | 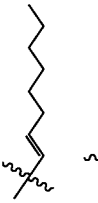 | H | H | H | H | H | H | 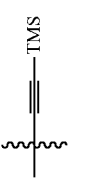 | H | H |
| 25 | H | H | 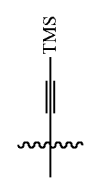 | H | H | H | H | H | H | 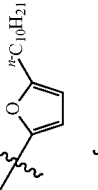 | H | H |
| 26 | H | H | 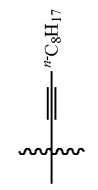 | H | H | H | H | H | H |  | H | H |

TABLE 1-continued

STRUCTURAL FORMULA

| Specific examples | R1 | R2 | R3 | R4 | R5 | R6 | R7 | R8 | R9 | R10 | R11 | R12 |
|---|---|---|---|---|---|---|---|---|---|---|---|---|
| 27 | H | H | *tert-octyl-like branched alkyl group* | H | H | H | H | H | H | *tert-octyl-like branched alkyl group* | H | H |
| 28 | H | H | 2-(n-C₁₀H₂₁)-thiazol-5-yl | H | H | H | H | H | H | 2-(n-C₁₀H₂₁)-thiazol-5-yl | H | H |
| 29 | H | H | n-C₁₀H₂₁-O-(CH₂)₄- | H | H | H | H | H | H | Ph | H | H |
| 30 | H | H | n-C₁₀H₂₁-O-(CH₂)₄- | H | H | H | H | H | H | Ph | H | H |
| 31 | H | H | H | n-C₁₀H₂₁ | H | H | H | H | n-C₁₀H₂₁ | H | H | H |
| 32 | H | H | H | n-C₉H₁₉ | H | H | H | H | n-C₉H₁₉ | H | H | H |
| 33 | H | H | H | n-C₈H₁₇ | H | H | H | H | n-C₈H₁₇ | H | H | H |
| 34 | H | H | H | n-C₇H₁₅ | H | H | H | H | n-C₇H₁₅ | H | H | H |
| 35 | H | H | H | n-C₆H₁₃ | H | H | H | H | n-C₆H₁₃ | H | H | H |
| 36 | H | H | H | n-C₅H₁₁ | H | H | H | H | n-C₅H₁₁ | H | H | H |
| 37 | H | H | H | n-C₄H₉ | H | H | H | H | n-C₄H₉ | H | H | H |
| 38 | H | H | H | n-C₃H₇ | H | H | H | H | n-C₃H₇ | H | H | H |
| 39 | H | H | H | n-C₁₁H₂₃ | H | H | H | H | n-C₁₁H₂₃ | H | H | H |
| 40 | H | H | H | n-C₁₂H₂₅ | H | H | H | H | n-C₁₂H₂₅ | H | H | H |
| 41 | H | H | H | Et | H | H | H | H | Et | H | H | H |
| 42 | H | H | H | Me | H | H | H | H | Me | H | H | H |
| 43 | H | H | H | 4-(n-C₁₀H₂₁)-phenyl | H | H | H | H | 4-(n-C₁₀H₂₁)-phenyl | H | H | H |
| 44 | H | H | H | 5-(n-C₁₀H₂₁)-thiophen-2-yl | H | H | H | H | 5-(n-C₁₀H₂₁)-thiophen-2-yl | H | H | H |
| 45 | H | H | H | 3-(n-C₁₀H₂₁)-phenyl | H | H | H | H | 3-(n-C₁₀H₂₁)-phenyl | H | H | H |

TABLE 1-continued
| Specific examples | R1 | R2 | R3 | R4 | R5 | R6 | R7 | R8 | R9 | R10 | R11 | R12 |
|---|---|---|---|---|---|---|---|---|---|---|---|---|
| 46 | H | H | H |  | H | H | H | H | 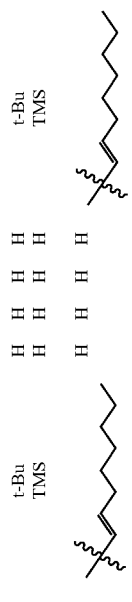 | H | H | H |
| 47 | H | H | H |  | H | H | H | H |  | H | H | H |
| 48 | H | H | H | t-Bu | H | H | H | H | t-Bu | H | H | H |
| 49 | H | H | H | TMS | H | H | H | H | TMS | H | H | H |
| 50 | H | H | H |  | H | H | H | H | 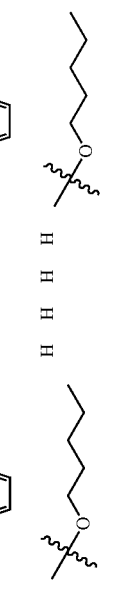 | H | H | H |
| 51 | H | H | H | n-C₈H₁₇ alkyne | H | H | H | H | n-C₈H₁₇ alkyne | H | H | H |
| 52 | H | H | H | pyridine-n-C₁₀H₂₁ | H | H | H | H | pyridine-n-C₁₀H₂₁ | H | H | H |
| 53 | H | H | H | selenophene-n-C₁₀H₂₁ | H | H | H | H | selenophene-n-C₁₀H₂₁ | H | H | H |
| 54 | H | H | H | furan-n-C₁₀H₂₁ | H | H | H | H | furan-n-C₁₀H₂₁ | H | H | H |
| 55 | H | H | H |  | H | H | H | H |  | H | H | H |
| 56 | H | H | H | TMS alkyne | H | H | H | H | TMS alkyne | H | H | H |

TABLE 1-continued

| Specific examples | R1 | R2 | R3 | R4 | R5 | R6 | R7 | R8 | R9 | R10 | R11 | R12 |
|---|---|---|---|---|---|---|---|---|---|---|---|---|
| 57 | H | H | H | (2,4,4-trimethylpentan-2-yl) | H | H | H | H | (2,4,4-trimethylpentan-2-yl) | H | H | H |
| 58 | H | H | H | 5-(n-C$_{10}$H$_{21}$)-thiazol-2-yl | H | H | H | H | 5-(n-C$_{10}$H$_{21}$)-thiazol-2-yl | H | H | H |
| 59 | H | H | H | n-C$_{10}$H$_{21}$ | H | H | H | H | n-C$_{10}$H$_{21}$ | H | H | H |
| 60 | H | H | H | (branched alkoxy) | H | H | H | H | (branched alkoxy) | H | H | H |
| 61 | H | n-C$_{10}$H$_{21}$ | H | H | H | H | H | H | H | H | n-C$_{10}$H$_{21}$ | H |
| 62 | H | n-C$_9$H$_{19}$ | H | H | H | H | H | H | H | H | n-C$_9$H$_{19}$ | H |
| 63 | H | n-C$_8$H$_{17}$ | H | H | H | H | H | H | H | H | n-C$_8$H$_{17}$ | H |
| 64 | H | n-C$_7$H$_{15}$ | H | H | H | H | H | H | H | H | n-C$_7$H$_{15}$ | H |
| 65 | H | n-C$_6$H$_{13}$ | H | H | H | H | H | H | H | H | n-C$_6$H$_{13}$ | H |
| 66 | H | n-C$_5$H$_{11}$ | H | H | H | H | H | H | H | H | n-C$_5$H$_{11}$ | H |
| 67 | H | n-C$_4$H$_9$ | H | H | H | H | H | H | H | H | n-C$_4$H$_9$ | H |
| 68 | H | n-C$_3$H$_7$ | H | H | H | H | H | H | H | H | n-C$_3$H$_7$ | H |
| 69 | H | n-C$_{11}$H$_{23}$ | H | H | H | H | H | H | H | H | n-C$_{11}$H$_{23}$ | H |
| 70 | H | n-C$_{12}$H$_{25}$ | H | H | H | H | H | H | H | H | n-C$_{12}$H$_{25}$ | H |
| 71 | H | Et | H | H | H | H | H | H | H | H | Et | H |
| 72 | H | Me | H | H | H | H | H | H | H | H | Me | H |
| 73 | H | 4-(n-C$_{10}$H$_{21}$)phenyl | H | H | H | H | H | H | H | H | 4-(n-C$_{10}$H$_{21}$)phenyl | H |

TABLE 1-continued

STRUCTURAL FORMULA

| Specific examples | R1 | R2 | R3 | R4 | R5 | R6 | R7 | R8 | R9 | R10 | R11 | R12 |
|---|---|---|---|---|---|---|---|---|---|---|---|---|
| 74 | H | 2-(n-C$_{10}$H$_{21}$)-thiophen-5-yl | H | H | H | H | H | H | H | H | 2-(n-C$_{10}$H$_{21}$)-thiophen-5-yl | H |
| 75 | H | 3-(n-C$_{10}$H$_{21}$)-phenyl | H | H | H | H | H | H | H | H | 3-(n-C$_{10}$H$_{21}$)-phenyl | H |
| 76 | H | 4-(n-C$_{10}$H$_{21}$)-thiophen-2-yl | H | H | H | H | H | H | H | H | 4-(n-C$_{10}$H$_{21}$)-thiophen-2-yl | H |
| 77 | H | −(CH$_2$)$_3$−O−(CH$_2$)$_3$−CH$_3$ | H | H | H | H | H | H | H | H | −(CH$_2$)$_3$−O−(CH$_2$)$_3$−CH$_3$ | H |
| 78 | H | t-Bu | H | H | H | H | H | H | H | H | t-Bu | H |
| 79 | H | TMS | H | H | H | H | H | H | H | H | TMS | H |
| 80 | H | alkenyl chain | H | H | H | H | H | H | H | H | alkenyl chain | H |
| 81 | H | −C≡C−n-C$_8$H$_{17}$ | H | H | H | H | H | H | H | H | −C≡C−n-C$_8$H$_{17}$ | H |
| 82 | H | 2-(n-C$_{10}$H$_{21}$)-pyridin-5-yl | H | H | H | H | H | H | H | H | 2-(n-C$_{10}$H$_{21}$)-pyridin-5-yl | H |

TABLE 1-continued
STRUCTURAL FORMULA
| Specific examples | R1 | R2 | R3 | R4 | R5 | R6 | R7 | R8 | R9 | R10 | R11 | R12 |
|---|---|---|---|---|---|---|---|---|---|---|---|---|
| 83 | H | 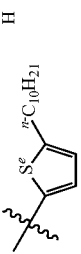 | H | H | H | H | H | H | H | H | 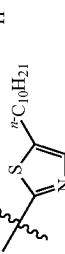 | H |
| 84 | H |  | H | H | H | H | H | H | H | H |  | H |
| 85 | H | 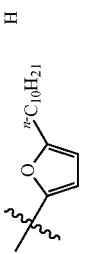 | H | H | H | H | H | H | H | H |  | H |
| 86 | H | 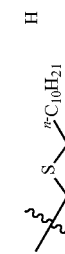 | H | H | H | H | H | H | H | H |  | H |
| 87 | H |  | H | H | H | H | H | H | H | H |  | H |
| 88 | H |  | H | H | H | H | H | H | H | H |  | H |

TABLE 1-continued

| Specific examples | R1 | R2 | R3 | R4 | R5 | R6 | R7 | R8 | R9 | R10 | R11 | R12 |
|---|---|---|---|---|---|---|---|---|---|---|---|---|
| | | | | | | | | | | | STRUCTURAL FORMULA | |
| 89 | H | n-C$_{10}$H$_{21}$ | H | H | H | H | H | H | H | H | n-C$_{10}$H$_{21}$ | H |
| 90 | H | —O—(CH$_2$)$_4$—n-C$_{10}$H$_{21}$ | H | H | H | H | H | H | H | H | —O—(CH$_2$)$_4$—n-C$_{10}$H$_{21}$ | H |
| 91 | H | H | n-C$_{10}$H$_{21}$ | H | H | H | H | H | H | n-C$_{10}$H$_{21}$ | H | H |
| 92 | H | H | n-C$_6$H$_{13}$ | H | H | H | H | H | H | n-C$_6$H$_{13}$ | H | H |
| 93 | H | H | 4-(n-C$_{10}$H$_{21}$)-phenyl | H | H | H | H | H | H | 4-(n-C$_{10}$H$_{21}$)-phenyl | H | H |
| 94 | H | H | 5-(n-C$_{10}$H$_{21}$)-thien-2-yl | H | H | H | H | H | H | 5-(n-C$_{10}$H$_{21}$)-thien-2-yl | H | H |
| 95 | H | H | 3-(n-C$_{10}$H$_{21}$)-phenyl | H | H | H | H | H | H | 3-(n-C$_{10}$H$_{21}$)-phenyl | H | H |
| 96 | H | H | 4-(n-C$_{10}$H$_{21}$)-thien-2-yl | H | H | H | H | H | H | 4-(n-C$_{10}$H$_{21}$)-thien-2-yl | H | H |

Structural formula: dibenzo[b,d]tellurophene-fused naphthalene core with substituents R$_1$–R$_{12}$ at positions around the three fused aromatic rings, the central heteroatom being Te.

The method for synthesizing the compound represented by General Formula (1) is not particularly limited, and the compound can be synthesized with reference to well-known methods.

Preferred examples of the synthesis method include a method including a step of heating and reacting a compound represented by General Formula (3) and a compound represented by General Formula (4) in the presence of a transition metal catalyst and an organic solvent.

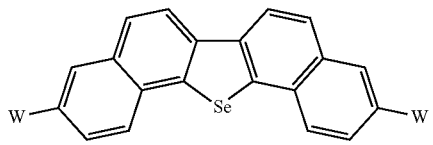

General Formula (3)

In General Formula (3),

W's each independently represents a halogen atom or a perfluoroalkylsulfonyloxy group.

General Formula (4)

In General Formula (4), $R^{11}$ represents an alkyl group, an alkenyl group, an alkynyl group, an aryl group, or a heteroaryl group and may further have a substituent, M represents magnesium, silicon, boron, tin, or zinc, $R^{12}$'s each independently represent a halogen atom an alkyl group, an alkenyl group, an alkynyl group, an alkoxy group, or a hydroxyl group, may be identical to or different from one another, and may form a ring in association with one another, and i represents an integer of 1 to 3, is one smaller than the valence of M; however, in a case in which M is boron, i may be 3.

The transition metal catalyst is not particularly limited, and it is possible to preferably use transition metal catalysts that are used in coupling reactions such as Kumada-Tamao-Corriu coupling, Hiyama coupling, Suzuki-Miyaura coupling, Migita-Kosugi-Stille coupling, Sonogashira-Hagihara coupling, Mizoroki-Heck reactions, or Negishi coupling. Among them, palladium catalysts or nickel catalysts are preferred, and palladium catalysts are more preferred. In addition, the metal catalyst may have an arbitrary ligand depending on reactions.

The organic solvent is not particularly limited and can be appropriately selected depending on matrixes or the catalyst.

In addition, the amounts of the compounds represented by General Formulae (3) and (4), the transition metal catalyst, and the organic solvent used are not particularly limited and may be appropriately selected as necessary.

The heating temperature during reactions is not particularly limited, but is preferably 25° C. to 200° C. and more preferably 40° C. to 150° C.

The number of kinds of the compound represented by General Formula (1) included in the organic semiconductor film of the organic thin-film transistor of the present invention may be one or more, but is preferably one from the viewpoint of the orientation.

In addition, the number of kinds of the compound represented by General Formula (1) included in an organic semiconductor film, a material for an organic thin-film transistor, or a composition for an organic thin-film transistor described below may be one or more, but is preferably one from the viewpoint of the orientation.

The total content of the compound represented by General Formula (1) in the organic semiconductor film of the organic thin-film transistor of the present invention is preferably 30% to 100% by mass, more preferably 50% to 100% by mass, and still more preferably 70% to 100% by mass. In addition, in the case of containing no binder polymer described below, the total content is preferably 90% to 100% by mass and more preferably 95% to 100% by mass.

<Structure of Organic Thin-Film Transistor and Method for Manufacturing Organic Thin-Film Transistor>

Next, the structure of the organic thin-film transistor of the present invention in which the compound represented by General Formula (1) is used in the organic semiconductor film of the organic thin-film transistor and a manufacturing method therefor will be described.

The organic thin-film transistor of the present invention has the organic semiconductor film (organic semiconductor layer) including the compound represented by General Formula (1) and may further have a source electrode, a drain electrode, and a gate electrode.

The structure of the organic thin-film transistor according to the present invention is not particularly limited and may be any structure of, for example, a bottom contact-type (bottom contact-bottom gate-type and bottom contact-top gate-type) structure, a top contact-type (top contact-bottom gate-type and top contact-top gate-type) structure, or the like.

Hereinafter, an example of the organic thin-film transistor of the present invention will be described with reference to the drawings.

FIG. 1 is a schematic cross-sectional view of a bottom contact-type organic thin-film transistor 100 according to an embodiment of the present invention.

In the example of FIG. 1, the organic thin-film transistor 100 has a substrate (base material) 10, a gate electrode 20, a gate insulating film 30, a source electrode 40, a drain electrode 42, an organic semiconductor film (organic semiconductor layer) 50, and a sealing layer 60. Here, the organic semiconductor film 50 is produced using the compound represented by General Formula (1).

Hereinafter, the substrate (base material), the gate electrode, the gate insulating film, the source electrode, the drain electrode, the organic semiconductor film (organic semiconductor layer), and the sealing layer and production methods therefor will be described in detail.

(Substrate)

The substrate plays a role of supporting the gate electrode, the source electrode, the drain electrode, all of which will be described below, or the like.

The kind of the substrate is not particularly limited, and examples thereof include a plastic substrate, a glass substrate, a ceramic substrate, and the like. Among these, from the viewpoint of applicability to individual devices and costs, a glass substrate or a plastic substrate is preferred.

(Gate Electrode)

The material of the gate electrode include metal such as gold (Au), silver, aluminum, copper, chromium, nickel, cobalt, titanium, platinum, magnesium, calcium, barium, and sodium; conductive oxides such as $InO_2$, $SnO_2$, and indium tin oxide (ITO); conductive macromolecules such as polyaniline, polypyrrole, polythiophene, polyacetylene, and polydiacetylene; semiconductors such as silicon, germanium, and gallium arsenide; carbon materials such as fullerene, carbon nanotubes, and graphite; and the like. Among these, metal is preferred, and silver or aluminum is more preferred.

The thickness of the gate electrode is not particularly limited, but is preferably 20 to 200 nm.

Meanwhile, the gate electrode may also function as the substrate, and, in such a case, the above-described substrate may not be provided.

The method for forming the gate electrode is not particularly limited, and examples thereof include a method in which an electrode material is deposited in a vacuum or sputtered on a substrate, a method in which a composition for forming the electrode is applied or printed, and the like. In addition, examples of the patterning method in the case of patterning the electrode include printing methods such as a photolithography method, ink jet printing, screen printing, offset printing, and anastatic printing (flexo printing); a mask deposition method; and the like.

(Gate Insulating Film)

Examples of the material for the gate insulating film include polymers such as polymethyl methacrylate, polystyrene, polyvinyl phenol, polyimide, polycarbonate, polyester, polyvinyl alcohol, polyvinyl acetate, polyurethane, polysulfone, polybenzoxazole, polysilsesquioxane, an epoxy resin, and a phenolic resin; oxides such as silicon dioxide, aluminum oxide, and titanium oxide; nitrides such as silicon nitride; and the like. Among these materials, polymers are preferred from the viewpoint of compatibility with the organic semiconductor film.

The film thickness of the gate insulating film is not particularly limited, but is preferably 100 to 1,000 nm.

The method for forming the gate insulating film is not particularly limited, and examples thereof include a method in which a composition for forming the gate insulating film is applied onto the substrate on which the gate electrode is formed, a method in which a gate insulating film material is deposited or sputtered, and the like.

(Source Electrode and Drain Electrode)

Specific examples of the material of the source electrode and the drain electrode are the same as those for the gate electrode. Among them, metal is preferred, and silver is more preferred.

The method for forming the source electrode and the drain electrode is not particularly limited, and examples thereof include a method in which an electrode material is deposited in a vacuum or sputtered on a substrate on which the gate electrode and the gate insulating film are formed, a method in which a composition for forming the electrode is applied or printed, and the like. Specific examples of the patterning method are the same as those for the gate electrode.

(Organic Semiconductor Film)

The method for producing the organic semiconductor film is not particularly limited as long as organic semiconductor films including the compound represented by General Formula (1) can be produced, and, for example, the organic semiconductor film can be produced by applying a composition for the organic thin-film transistor including the compound represented by General Formula (1) (described below) on a substrate and drying the composition.

Meanwhile, the application of the composition for the organic thin-film transistor onto a substrate refers not only to an aspect in which the composition for the organic thin-film transistor is directly imparted to a substrate but also to an aspect in which the composition for the organic thin-film transistor is imparted above a substrate through a separate layer provided on the substrate.

As the method for applying the composition for the organic thin-film transistor, well-known methods can be used, and examples thereof include a bar coating method, a spin coating method, a knife coating method, a doctor blade method, an ink jet printing method, a flexo printing method, a gravure printing method, and a screen printing method.

Furthermore, as the method for applying the composition for the organic thin-film transistor, the method for forming the organic semiconductor film described in JP2013-207085A (a so-called gap cast method), the method for manufacturing the organic semiconductor film described in WO2014/175351A (a so-called edge cast method or continuous edge cast method), or the like is preferably used.

For drying (drying treatment), the optimal conditions are appropriately selected depending on the kinds of individual components included in the composition for the organic thin-film transistor, and the composition may be naturally dried, but is preferably heated from the viewpoint of improving productivity. For example, the heating temperature is preferably 30° C. to 200° C. and more preferably 40° C. to 150° C., and the heating time is preferably 10 to 300 minutes and more preferably 30 to 180 minutes.

The film thickness of the organic semiconductor film being produced is not particularly limited, but is preferably 10 to 500 nm and more preferably 20 to 200 nm since the effects of the present invention are more favorable.

As described above, the organic semiconductor film containing the compound represented by General Formula (1) is preferably used in the organic thin-film transistor, but the use thereof is not limited thereto, and the organic semiconductor film containing the compound represented by General Formula (1) can also be applied to other uses described below.

(Sealing Layer)

From the viewpoint of durability, the organic thin-film transistor of the present invention preferably includes a sealing layer in the outermost layer. For the sealing layer, a well-known sealing agent (composition for forming the sealing layer) can be used.

The thickness of the sealing layer is not particularly limited, but is preferably 0.2 to 10 μm.

(Other Organic Thin-Film Transistors)

Figure 2:
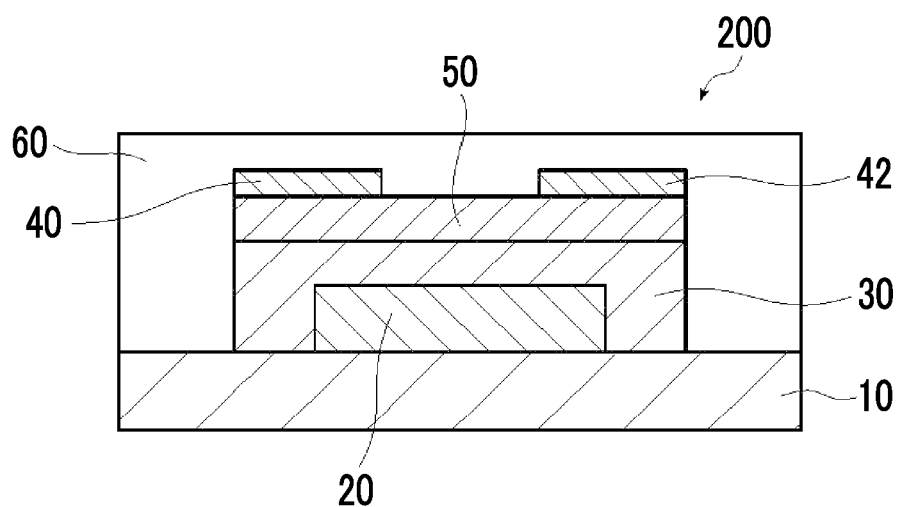
FIG. 2 is a schematic cross-sectional view of a top contact-type organic thin-film transistor according to an embodiment of the present invention.

FIG. 2 is a schematic cross-sectional view of a top contact-type organic thin-film transistor 200 according to an embodiment of the present invention.

In the example of FIG. 2, the organic thin-film transistor 200 has the substrate 10, the gate electrode 20, the gate insulating film 30, the source electrode 40, the drain electrode 42, the organic semiconductor film (organic semiconductor layer) 50, and the sealing layer 60. Here, the organic semiconductor film 50 is formed using a composition for an organic thin-film transistor of the present invention described below.

The substrate, the gate electrode, the gate insulating film, the source electrode, the drain electrode, the organic semiconductor film, and the sealing layer have already been described above and thus will not be described again.

(Applications of Organic Thin-Film Transistor)

The organic thin-film transistor can be singly used as switching elements. In addition, the organic thin-film transistor can be used for, for example, electronic paper, display portions that display images of display devices, light-receiving portions that receive the light of images of X-ray flat panel detectors, and the like by arraying a plurality of elements on a matrix. In addition, the organic thin-film transistor can be applied to small-sized circuits such as inverters, ring oscillators, and d-flip-flops or logic circuits such as radio frequency identifiers (RFID, RF tags) or memories by combining a plurality of elements. The respective devices may have a well-known structure, and thus the structures thereof will not be described.

[Composition for Organic Thin-Film Transistor]

A composition for an organic thin-film transistor of the present invention is used to produce the organic semiconductor film of the organic thin-film transistor.

Meanwhile, the composition for an organic thin-film transistor which will be described below may be used for other uses described below, and, in such cases, the "composition for an organic thin-film transistor" will be simply referred to as "organic semiconductor composition".

The composition for an organic thin-film transistor contains the compound represented by General Formula (1) and, generally, further contains an organic solvent from the viewpoint of improving the coatability.

In the case of containing an organic solvent, the content thereof is preferably 0.01% to 80% by mass, more preferably 0.05% to 10% by mass, and still more preferably 0.1% to 5% by mass with respect to the total mass of the composition for an organic thin-film transistor from the viewpoint of improving the coatability.

(Organic Solvent)

The organic solvent is not particularly limited, and examples thereof include hydrocarbon-based solvents such as hexane, octane, decane, toluene, xylene, mesitylene, ethylbenzene, decalin, tetralin, 2-methyl benzothiazole, and 1-methyl naphthalene, ketone-based solvents such as acetone, methyl ethyl ketone, methyl isobutyl ketone, and cyclohexanone, halogenated hydrocarbon-based solvents such as dichloromethane, chloroform, tetrachloromethane, dichloroethane, trichloroethane, tetrachloroethane, chlorobenzene, dichlorobenzene, 1,2-dichlorobenzene, I-fluoronaphthalene, 2,5-dichlorothiophene, 2,5-dibromothiophene, 1-chloronaphthalene, and chlorotoluene, ester-based solvents such as ethyl acetate, butyl acetate, amyl acetate, and ethyl lactate, alcohol-based solvents such as methanol, propanol, butanol, pentanol, hexanol, cyclohexanol, methyl cellosolve, ethyl cellosolve, and ethylene glycol, ether-based solvents such as butoxybenzene, dibutyl ether, tetrahydrofuran, dioxane, and anisole, amide-based solvents such as N,N-dimethyl formamide and N,N-dimethylacetamide, imide-based solvents such as 1-methyl-2-pyrrolidone and 1-methyl-2-imidazolidinone, sulfoxide-based solvents such as dimethyl sulfoxide, nitrile-based solvents such as acetonitrile, and the like.

The organic solvent may be used singly or two or more solvents may be jointly used.

(Binder Polymer)

The composition for an organic thin-film transistor may further contain a binder polymer.

The kind of the binder polymer is not particularly limited, and well-known binder polymers can be used. Examples of the binder polymer include insulating polymers such as polystyrene, polycarbonate, polyarylate, polyester, polyamide, polyimide, polyurethane, polysiloxane, polysulfone, polymethyl methacrylate, polymethyl acrylate, cellulose, polyethylene, and polypropylene and copolymers thereof; rubber or thermoplastic elastomers such as ethylene-propylene rubber, acrylonitrile-butadiene rubber, hydrogenated nitrile rubber, fluororubber, a perfluoroelastomer, a tetrafluoroethylene propylene copolymer, an ethylene-propylene-diene copolymer, styrene-butadiene rubber, polychloroprene, polyneoprene, butyl rubber, a methyl phenyl silicone resin, a methyl phenyl vinyl silicone resin, a methyl vinyl silicone resin, a fluorosilicone resin, acrylic rubber, ethylene acrylic rubber, chlorosulfonated polyethylene, chloropolyethylene, an epichlorohydrin copolymer, a polyisoprene-natural rubber copolymer, polyisoprene rubber, a styrene-isoprene block copolymer, a polyether urethane copolymer, a polyether ester thermoplastic elastomer, and polybutadiene rubber, photoconductive polymers such as polyvinyl carbazole and polysilane; conductive polymers such as polythiophene, polypyrrole, polyaniline, and polyparaphenylene vinylene; and semiconductor polymers described in, for example, Chemistry of Materials, 2014, 26, 647.

The polymer binder may be used singly or a plurality of polymer binders may be jointly used.

Among these, the binder polymer is preferably a macromolecular compound having a benzene ring (a macromolecule having a monomer unit having a benzene ring). The content of the monomer unit having a benzene ring is not particularly limited, but is preferably 50% by mole or more, more preferably 70% by mole or more, and still more preferably 90% by mole or more. The upper limit is not particularly limited, but is, for example, 100% by mole.

Specific examples of the binder polymer include polystyrene, poly($\alpha$-methylstyrene), polyvinyl cinnamate, poly(4-vinylphenyl), poly(4-methylstyrene), poly[bis(4-phenyl)(2,4,6-trimethylphenyl)amine], and poly[2,6-(4,4-bis(2-ethylhexyl)-4Hcyclopenta[2,1-b;3,4-b']dithiophene)-alt-4,7-(2,1,3-benzothiazole)], and the like, polystyrene or poly($\alpha$-methylstyrene) is more preferred, and poly($\alpha$-methylstyrene) is still more preferred.

The weight-average molecular weight of the binder polymer is not particularly limited, but is preferably 1,000 to 2,000,000, more preferably 3,000 to 1,000,000, and still more preferably 5,000 to 600,000.

In the case of containing the binder polymer, the content is preferably 1 to 10,000 parts by mass, more preferably 10 to 1.000 parts by mass, still more preferably 25 to 400 parts by mass, and most preferably 50 to 200 parts by mass with respect to 100 parts by mass of the compound represented by General Formula (1) included in the composition for an organic thin-film transistor. In the above-described range, the carrier mobility of organic semiconductor films and organic semiconductor elements to be obtained and the uniformity of films are superior.

(Other Components)

The composition for an organic thin-film transistor may contain components other than the components described above. As the other components, well-known additives and the like can be used.

(Preparation Method)

The method for preparing the composition for an organic thin-film transistor is not particularly limited and well-known methods can be used. For example, a predetermined amount of the compound represented by General Formula (1) and the like are added to the organic solvent, and a stirring treatment is appropriately carried out, whereby the composition for an organic thin-film transistor of the present invention can be obtained.

[Material for Organic Thin-Film Transistor]

A material for an organic thin-film transistor of the present invention contains the compound represented by General Formula (1). The material for an organic thin-film transistor refers to a material which is used for organic thin-film transistors and exhibits the characteristics of semiconductors.

The compound represented by General Formula (1) is a material exhibiting the properties of semiconductors and is a p-type (hole transport-type) organic semiconductor material that conducts electricity using electrons as carriers.

Meanwhile, the material for an organic thin-film transistor may be used for other uses described below, and, in such cases, the "material for an organic thin-film transistor" will be simply referred to as "organic semiconductor material".

[Other Uses of Compound Represented by General Formula (1)]

The compound represented by General Formula (1) has excellent properties as described above and thus can also be preferably used for uses other than organic thin-film transistors.

Examples of the other uses include non-luminous organic semiconductor devices. The non-luminous organic semiconductor devices refer to devices that are not intended to emit light.

Examples of the non-luminous organic semiconductor devices include, in addition to the above-described organic thin-film transistor, organic photoelectric conversion elements (solid image pickup elements for light sensors, solar batteries for energy conversion, and the like), gas sensors, organic rectifier cells, information recording elements, and the like.

In the non-luminous organic semiconductor devices, the organic semiconductor film is preferably caused to function as an electronics element. The scope of the organic semiconductor film includes organic semiconductor films including the compound represented by General Formula (1).

EXAMPLES

Hereinafter, the characteristics of the present invention will be more specifically described using examples and comparative examples. Materials, amounts used, proportions, processing contents, processing orders, and the like described in the following examples can be appropriately modified within the scope of the gist of the present invention. Therefore, the scope of the present invention is not supposed to be restrictively interpreted by specific examples described below.

Examples 1-1 to 1-8 and Comparative Examples 1-1 to 1-4

<Synthesis of Compound 1>

A compound 1 which is the compound represented by General Formula (1) was synthesized according to a specific synthesis order illustrated in the following scheme.

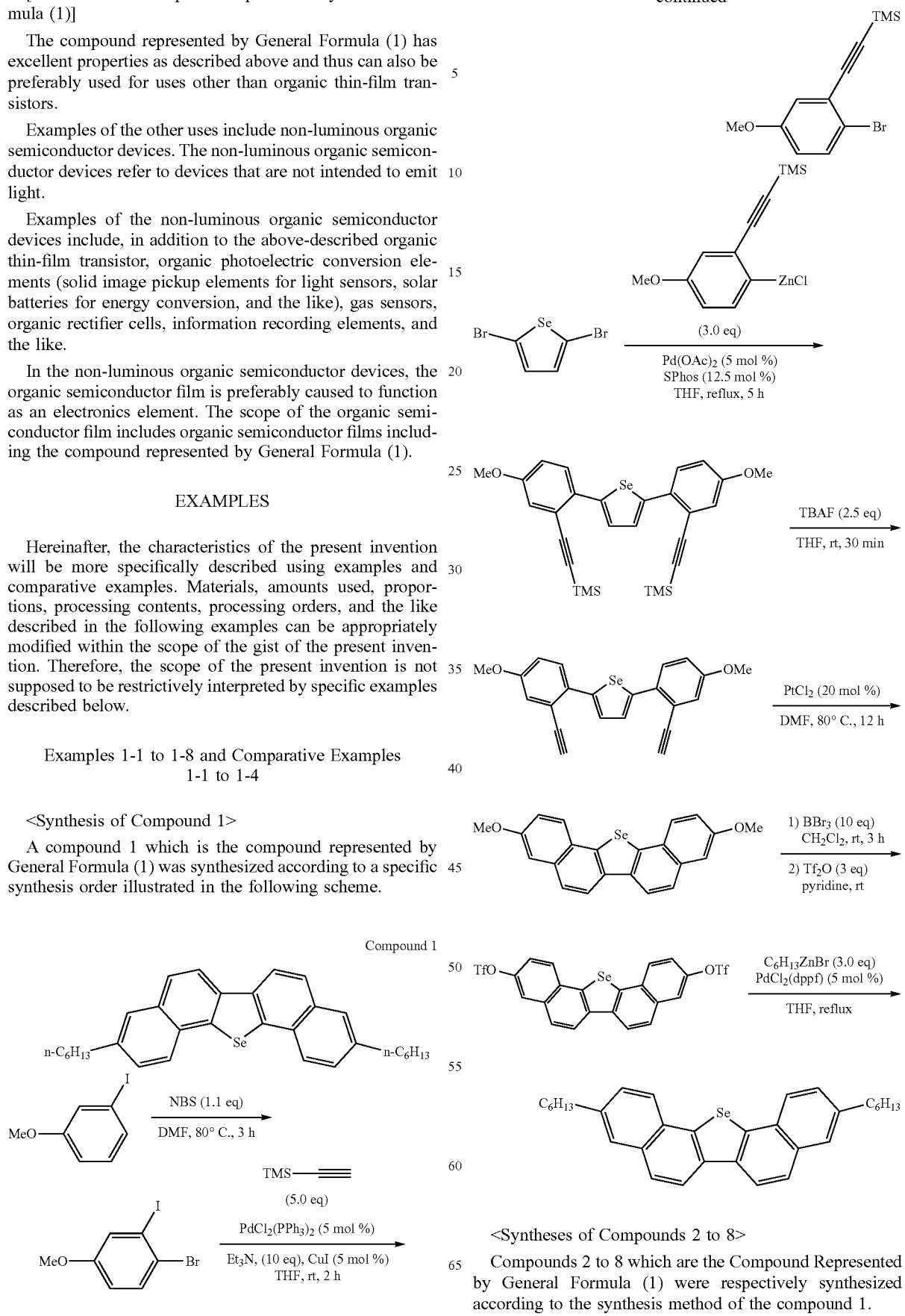

<Syntheses of Compounds 2 to 8>

Compounds 2 to 8 which are the Compound Represented by General Formula (1) were respectively synthesized according to the synthesis method of the compound 1.

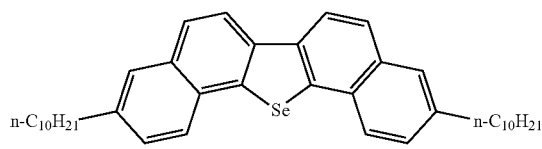

Compound 2

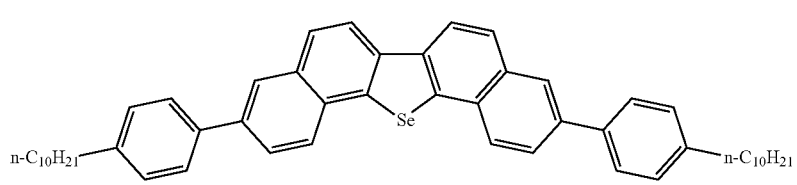

Compound 3

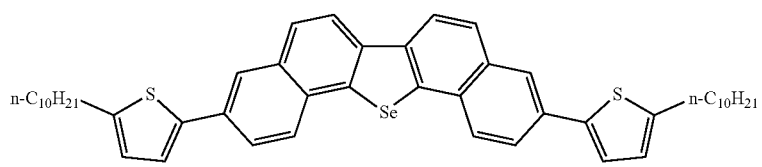

Compound 4

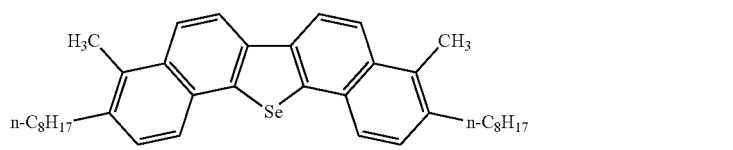

Compound 5

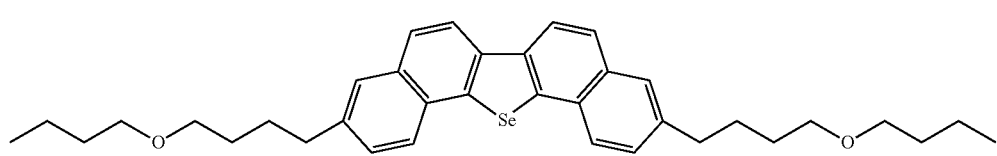

Compound 6

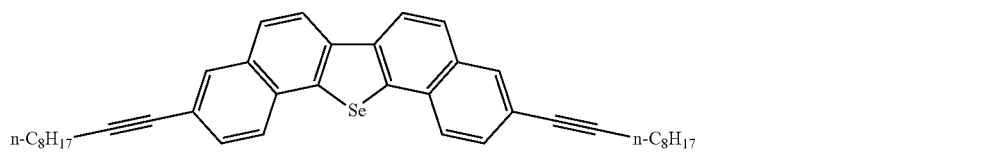

Compound 7

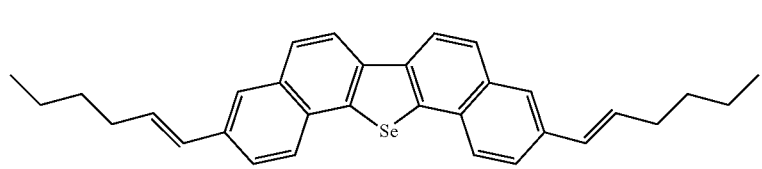

Compound 8

<Syntheses of Comparative Compounds 1 to 4>

Comparative compounds 1 to 4 that were used for organic semiconductor layers in comparative elements were synthesized according to methods described in individual documents. The structures of the comparative compounds 1 to 4 will be illustrated below.

Comparative compound 1

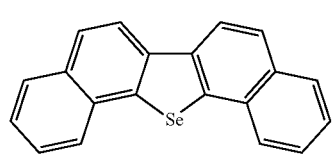

-continued

Comparative compound 2

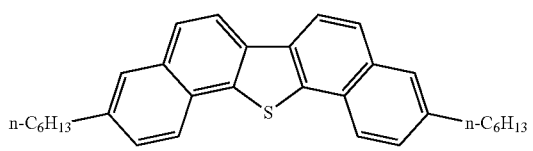

Comparative compound 3

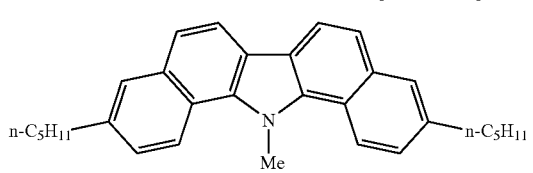

-continued

Comparative compound 4

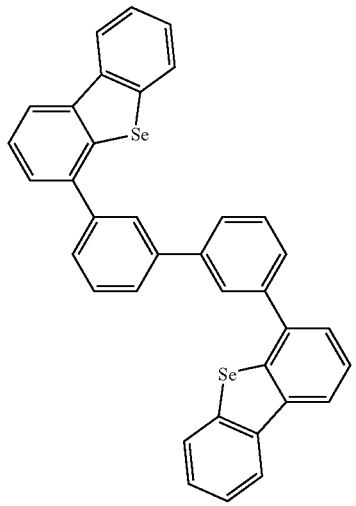

Meanwhile, a comparative compound 1 having the above-described structure was synthesized according to the synthesis method described in Chem. Mater., 2013, 25 (20), pp. 3952 to 3956. A comparative compound 2 having the above-described structure was the compound described in JP2015-48346A and was synthesized using the synthesis method described in JP2015-48346A. In addition, a comparative compound 3 having the above-described structure was the compound described in JP2014-168059A and was synthesized using the synthesis method described in JP2014-168059A. A comparative compound 4 having the above-described structure was the compound described in JP2012-503889A and was synthesized using the synthesis method described in JP2012-503889A.

<<Production and Evaluation of Elements>>

For the materials for an organic thin-film transistor used to produce elements (the respective compounds described above), the purities (the absorption intensity area ratio at 254 nm) were confirmed to be 99.0% or higher by means of high-speed liquid chromatography (TSKgel ODS-100Z manufactured by Tosoh Corporation).

<Production of Bottom Gate-Top Contact-Type Element by Coating Process>

The compound 1 synthesized above and toluene as a solvent were mixed together so as to prepare 0.1% by mass of a solution, and the solution was heated to 40° C. thereby producing a composition for an organic thin-film transistor 1.

In addition, compositions for an organic thin-film transistor 2 to 8 and compositions for an organic thin-film transistor for comparison 1 to 4 were respectively prepared using the same method except for the fact that any one of the compounds 2 to 8 or the comparative compounds 1 to 4 was used instead of the compound 1.

Figure 3:
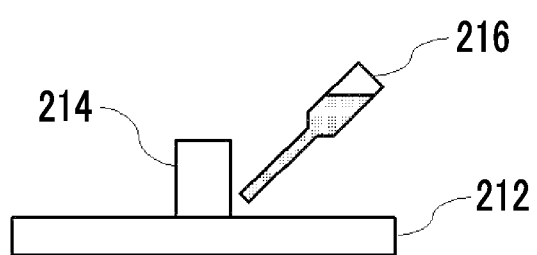
FIG. 3 is a schematic view illustrating a step of a method for manufacturing an organic semiconductor film in examples and comparative examples.
Figure 4A:
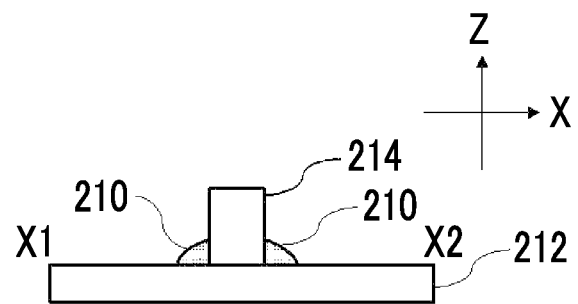
FIG. 4A is a schematic view illustrating a step of the method for manufacturing an organic semiconductor film in the examples and the comparative examples.
Figure 4B:
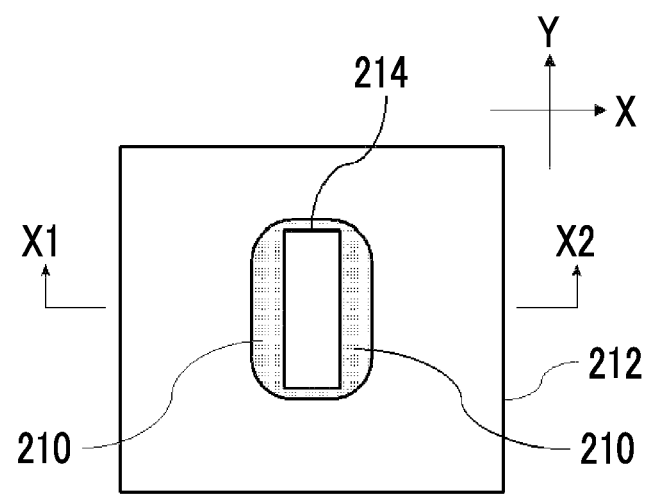
FIG. 4B is a schematic view illustrating a step of the method for manufacturing an organic semiconductor film in the examples and the comparative examples.
Figure 5:
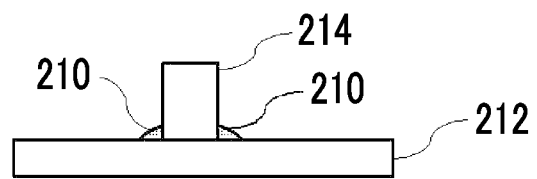
FIG. 5 is a schematic view illustrating a step of the method for manufacturing an organic semiconductor film in the examples and the comparative examples.

In the example and the comparative examples, organic semiconductor films were formed using the method illustrated in FIG. 3 to FIG. 5. FIG. 3 to FIG. 5 are schematic views illustrating a method for manufacturing the organic semiconductor films of the examples and the comparative examples.

The method for forming the organic semiconductor film will be described in detail using a case in which the composition for an organic thin-film transistor 1 was used as an example.

A 10 mm×10 mm substrate obtained by forming a 500 nm-thick $SiO_2$ thermally oxidized film on the surface of an n-type silicon substrate (thickness: 0.4 mm) was used as a substrate 212. The thermally oxidized film-side surface of the substrate 212 was washed with ultraviolet (UV)-ozone and then subjected to a 0-phenethyltrimethoxysilane treatment.

On the β-phenethyltrimethoxysilane-treated surface of the substrate 212, a member 214 was placed in the central portion of the substrate 212 as illustrated in FIG. 3 so as to come into contact with the substrate 212. As the member 214, a glass member having a length of 6 mm, a width of 1 mm, and a height of 2 mm was used. The horizontal direction (X-axis direction) in FIG. 3 is the width direction of the member 214, the vertical direction (Z-axis direction) in FIG. 3 is the height direction of the member 214, and the vertical direction (Y-axis direction) in FIG. 4B is the length direction of the member 214.

The substrate 212 was heated to 40° C., and one droplet (approximately 0.02 ml) of the composition for an organic thin-film transistor 1 (a composition for an organic thin-film transistor 210 illustrated in FIGS. 3 to 5) prepared using the above-described method was dropped on the substrate using a pipette 216 through a side portion of the member 214 so as to come into contact with both the substrate 212 and the member 214 as illustrated in FIG. 3, thereby adding the composition for an organic thin-film transistor 1 dropwise to a portion on the surface of the substrate 212 as illustrated in FIG. 4A and FIG. 4B. A concave meniscus was formed in the interface with the member 214.

The dropwise-added composition for an organic thin-film transistor 1 was naturally dried in a state in which the substrate 212 and the member 214 were in contact with each other and the positional relationship between the substrate 212 and the member 214 was fixed as illustrated in FIG. 5. After that, the composition was dried at a reduced pressure of $10^{-3}$ MPa and 30° C. for eight hours so as to precipitate the crystals of Compound 1, thereby forming an organic semiconductor film. Whether or not crystals were precipitated was checked by means of observation using a polarization microscope. Meanwhile, the film thickness of the obtained organic semiconductor film was 70 nm.

Furthermore, a mask was worn on the obtained organic semiconductor film, and a 2 nm-thick 2,3,5,6-tetrafluoro-7,7,8,8-tetracyanoquinodimethan (F4-TCNQ) as a charge injection acceptor and a 40 nm-thick metal electrode were respectively deposited thereon, thereby obtaining an organic thin-film transistor element 1 for measuring field-effect transistor (FET) characteristics (hereinafter, also referred to as "element 1").

In addition, organic thin-film transistor elements 1-2 to 1-8 (hereinafter, also referred to as "elements 1-2 to 1-8") and comparative organic thin-film transistor elements 1-1 to 1-4 (hereinafter, also referred to as "comparative elements 1-1 to 1-4") were respectively produced according to the method for producing the element 1 except for the fact that any one of the compositions for an organic thin-film transistor 2 to 8 and the compositions for an organic thin-film transistor for comparison 1 to 4 was used instead of the composition for an organic thin-film transistor 1. The obtained elements 1-1 to 1-8 and the comparative elements 1-1 to 1-4 were considered as organic thin-film transistors of Examples 1-1 to 1-8 and Comparative Examples 1-1 to 1-4.

<Evaluation>

The FET characteristics of each of the organic thin-film transistor elements (the elements 1-1 to 1-8 and the comparative elements 1-1 to 1-4) were evaluated from the viewpoint of carrier mobility at normal pressure in the atmosphere using a semiconductor parameter analyzer (manufactured by Agilent, 4156C) to which a semi-auto prober (manufactured by Vector Semiconductor Co., Ltd., AX-2000) was connected.

(Carrier Mobility)

A voltage of −50 V was applied between a source electrode and a drain electrode in each of the organic thin-film transistor element (FET element), the gate voltage was changed in a range of 20 V to −150 V, and the carrier mobility μ was computed using an expression expressing the drain current $I_d=(w/2L)\mu C_i(V_g-V_{th})^2$ (in the expression, L represents the gate length, W represents the gate width, $C_i$ represents the capacity of an insulating layer per unit area, $V_g$ represents the gate voltage, and $V_{th}$ represents the threshold voltage) and evaluated using the following five levels.

The obtained results are shown in the following table.

"AA": ≥4 cm$^2$/Vs
"A": ≥2 cm$^2$Ns or more to less than 4 cm$^2$/Vs
"B": 1 cm$^2$/Vs or more to less than 2 cm$^2$/Vs
"C": 0.1 cm$^2$/Vs or more to less than 1 cm$^2$/Vs
"D": <0.1 cm$^2$/Vs

TABLE 2

| | Element No. | Material for organic thin-film transistor | Carrier mobility (cm$^2$/Vs) |
|---|---|---|---|
| Example 1-1 | Element 1-1 | Compound 1 | AA |
| Example 1-2 | Element 1-2 | Compound 2 | AA |
| Example 1-3 | Element 1-3 | Compound 3 | AA |
| Example 1-4 | Element 1-4 | Compound 4 | AA |
| Example 1-5 | Element 1-5 | Compound 5 | A |
| Example 1-6 | Element 1-6 | Compound 6 | A |
| Example 1-7 | Element 1-7 | Compound 7 | AA |
| Example 1-8 | Element 1-8 | Compound 8 | A |
| Comparative Example 1-1 | Comparative element 1-1 | Comparative compound 1 | D |
| Comparative Example 1-2 | Comparative element 1-2 | Comparative compound 2 | C |
| Comparative Example 1-3 | Comparative element 1-3 | Comparative compound 3 | D |
| Comparative Example 1-4 | Comparative element 1-4 | Comparative compound 4 | D |

Examples 2-1 to 2-8 and Comparative Examples 2-1 to 2-4

<<Production and Evaluation of Elements>>
<Production of Bottom Gate-Bottom Contact-Type Element by Coating Process>

In Examples 2-1 to 2-8 and Comparative Examples 2-1 to 2-4, bottom gate-bottom contact-type organic thin-film transistor elements were produced. The details will be described below.

The composition for an organic thin-film transistor 1 obtained by heating the toluene solution of 0.01% by mass of the compound 1 to 40° C. In Example 1 was cast (using a drop casting method) onto a substrate for measuring FET characteristics heated to 40° C., which will be described below, in a nitrogen atmosphere, thereby obtaining a non-luminous organic thin-film transistor element 2-1 (hereinafter, also referred to as "element 2-1").

As the substrate for measuring FET characteristics, a bottom gate and bottom contact-structured silicon substrate including chromium/gold disposed in a comb shape (gate width W: 100 mm, gate length L: 100 μm) as source and drain electrodes and SiO$_2$ (film thickness: 500 nm) as an insulating film was used.

Organic thin-film transistor elements 2-2 to 2-8 (hereinafter, also referred to as "elements 2-2 to 2-8") and comparative organic thin-film transistor elements 2-1 to 2-4 (hereinafter, also referred to as "comparative elements 2-1 to 2-4") were respectively produced according to the method for producing the element 2-1 except for the fact that any one of the compositions for an organic thin-film transistor 2 to 8 and the compositions for an organic thin-film transistor for comparison 3 and 4 was used instead of the composition for an organic thin-film transistor 1. The obtained elements 2-1 to 2-8 and the comparative elements 2-1 to 2-4 were considered as organic thin-film transistors of Examples 2-1 to 2-8 and Comparative Examples 2-1 to 2-4.

<Evaluation>

The FET characteristics of each of the organic thin-film transistor elements (the elements 2-1 to 2-8 and the comparative elements 2-1 to 2-4) were evaluated using the same method as in Example 1-1. The results are shown in the following table.

TABLE 3

| | Element No. | Material for organic thin-film transistor | Carrier mobility (cm$^2$/Vs) |
|---|---|---|---|
| Example 2-1 | Element 2-1 | Compound 1 | AA |
| Example 2-2 | Element 2-2 | Compound 2 | AA |
| Example 2-3 | Element 2-3 | Compound 3 | AA |
| Example 2-4 | Element 2-4 | Compound 4 | AA |
| Example 2-5 | Element 2-5 | Compound 5 | A |
| Example 2-6 | Element 2-6 | Compound 6 | A |
| Example 2-7 | Element 2-7 | Compound 7 | AA |
| Example 2-8 | Element 2-8 | Compound 8 | A |
| Comparative Example 2-1 | Comparative element 2-1 | Comparative compound 1 | C |
| Comparative Example 2-2 | Comparative element 2-2 | Comparative compound 2 | B |
| Comparative Example 2-3 | Comparative element 2-3 | Comparative compound 3 | D |
| Comparative Example 2-4 | Comparative element 2-4 | Comparative compound 4 | C |

Examples 3-1 to 3-7 and Comparative Examples 3-1 to 3-4

<<Production and Evaluation of Elements>>
<Production of Bottom Gate-Top Contact-Type Element by Deposition Process>

The oxidized film-side surface of the substrate 212 was washed with UV-ozone using the same method as in Example 1-1 and then subjected to a dodecyltrichlorosilane treatment.

On the dodecyltrichlorosilane-treated surface of the substrate 212, a film of the compound 1 was deposited and grown at a deposition rate of 0.05 nm/s so as to obtain a film thickness of 40 nm.

Furthermore, a mask was worn on the obtained organic semiconductor film, and a 2 nm-thick F4-TCNQ as a charge injection acceptor and a 40 nm-thick metal electrode were respectively deposited thereon, thereby obtaining an organic thin-film transistor element 3-1 for measuring FET characteristics (hereinafter, also referred to as "element 3-1").

Organic thin-film transistor elements 3-2 to 3-7 (hereinafter, also referred to as "elements 3-2 to 3-7") and comparative organic thin-film transistor elements 3-1 to 3-4 (hereinafter, also referred to as "comparative elements 3-1 to 3-4") were respectively produced using the same method as for the element 3-1 except for the fact that any one of the compounds 2, 4 to 8 and the comparative compounds 1 to 4 was used instead of the compound 1. The obtained elements 3-1 to 3-7 and the comparative elements 3-1 to 3-4 were considered as organic thin-film transistors of Examples 3-1 to 3-7 and Comparative Examples 3-1 to 3-4.

<Evaluation>

The FET characteristics of each of the organic thin-film transistor elements (the elements 3-1 to 3-7 and the comparative elements 3-1 to 3-4) were evaluated using the same method as in Example 1. The results are shown in the following table.

TABLE 4

| | Element No. | Material for organic thin-film transistor | Carrier mobility ($cm^2/Vs$) |
|---|---|---|---|
| Example 3-1 | Element 3-1 | Compound 1 | AA |
| Example 3-2 | Element 3-2 | Compound 2 | AA |
| Example 3-3 | Element 3-3 | Compound 4 | AA |
| Example 3-4 | Element 3-4 | Compound 5 | A |
| Example 3-5 | Element 3-5 | Compound 6 | A |
| Example 3-6 | Element 3-6 | Compound 7 | AA |
| Example 3-7 | Element 3-7 | Compound 8 | A |
| Comparative Example 3-1 | Comparative element 3-1 | Comparative compound 1 | C |
| Comparative Example 3-2 | Comparative element 3-2 | Comparative compound 2 | B |
| Comparative Example 3-3 | Comparative element 3-3 | Comparative compound 3 | D |
| Comparative Example 3-4 | Comparative element 3-4 | Comparative compound 4 | C |

From the above-described evaluation results, it was confirmed that, in the organic thin-film transistor elements of the respective examples for which the compound represented by General Formula (1) was used, the carrier mobility was high, and it was found that the compound represented by General Formula (1) can be preferably used as a material for an organic thin-film transistor.

In addition, from the comparison among the respective examples in which the compounds 1 to 8 were used (refer to Tables 2 and 4), it was found the compound represented by General Formula (1) imparted an excellent carrier mobility in all of the film-forming means and the transistor layer constitutions.

Meanwhile, it was found that, in all of the organic thin-film transistor elements in which the comparative compounds 1 to 4 that are not in the scope of General Formula (1) were used for the organic semiconductor layers as the material for an organic thin-film transistor, the carrier mobility was low.

Examples 4-1 to 4-8 and Comparative Examples 4-1 to 4-4

<Production of Bottom Gate-Bottom Contact-Type Element Using Polymer Binder>

A bottom gate-bottom contact-type organic thin-film transistor 4-1 (hereinafter, also referred to as "element 4-1") was produced in the same manner as in Example 2-1 except for the fact that a material containing the compound 1 and poly α-methylstyrene in a mass ratio of 1:1 (material 1') was used instead of the compound 1 in Example 2-1. Organic thin-film transistor elements 4-2 to 4-8 (hereinafter, also referred to as "elements 4-2 to 4-8") and comparative organic thin-film transistor elements 4-1 to 4-4 (hereinafter, also referred to as "comparative elements 4-1 to 4-4") were respectively produced using the same method except for the fact that, in the production of the elements 4-1, any one of the compounds 2 to 8 and the comparative compounds 1 to 4 was used instead of the compound 1. The obtained elements 4-1 to 4-8 and the comparative elements 4-1 to 4-4 were considered as organic thin-film transistors of Examples 4-1 to 4-8 and Comparative Examples 4-1 to 4-4.

<Evaluation>

The FET characteristics of each of the organic thin-film transistor elements (the elements 4-1 to 4-8 and the comparative elements 4-1 to 4-4) were evaluated using the same method as in Example 1. The results are shown in the following table.

TABLE 5

| | Element No. | Material for organic thin-film transistor | Carrier mobility ($cm^2/Vs$) |
|---|---|---|---|
| Example 4-1 | Element 4-1 | Material 1' | AA |
| Example 4-2 | Element 4-2 | Material 2' | AA |
| Example 4-3 | Element 4-3 | Material 3' | AA |
| Example 4-4 | Element 4-4 | Material 4' | AA |
| Example 4-5 | Element 4-5 | Material 5' | A |
| Example 4-6 | Element 4-6 | Material 6' | A |
| Example 4-7 | Element 4-7 | Material 7' | AA |
| Example 4-8 | Element 4-8 | Material 8' | A |
| Comparative Example 4-1 | Compantive element 4-1 | Compantive material 1' | C |
| Comparative Example 4-2 | Comparative element 4-2 | Comparative material 2' | B |
| Comparative Example 4-3 | Comparative element 4-3 | Comparative material 3' | D |
| Comparative Example 4-4 | Comparative element 4-4 | Comparative material 4' | C |

From Table 5, it was confirmed that, in the organic thin-film transistor elements of the respective examples for which the compound represented by General Formula (1) of the present invention was used, the carrier mobility was high even in the case of the bottom gate-bottom contact-type elements and the case of using the polymer binders, and it was found that the compound represented by General Formula (1) of the present invention can be preferably used as organic thin-film transistor materials.

Meanwhile, it was found that the organic thin-film transistor elements in which the comparative compounds 1 to 4 that are not in the scope of General Formula (1) were used for the organic semiconductor layers as the organic thin-film transistor material, the carrier mobility was low.

Examples 5-1 to 5-16

<<Production and Evaluation of Elements>>

<Production of Bottom Gate-Bottom Contact-Type Element by Printing Method>

—Ink Jet Method—

The compound 1 and tetralin as a solvent were mixed together so as to prepare 0.1% by mass of a solution, and the solution was considered as a composition for an organic thin-film transistor 21. In addition, compositions for an organic thin-film transistor 22 to 28 were prepared in the same manner except for the fact that the respective compounds 2 to 8 were used instead of the compound 1.

An organic semiconductor film was formed on the same bottom gate-bottom contact-type substrate for measuring FET characteristics as in Example 2-1 using the composition for an organic thin-film transistor 21 and an ink jet method, thereby obtaining a non-luminous organic thin-film transistor element 5-1 (hereinafter, also referred to as "element 5-1").

Meanwhile, the specific method for producing the organic semiconductor film using the ink jet method is as described below.

As an ink jet apparatus, a 10 pl head of DMP2831 (manufactured by Fuji Graphic Systems) was used, and a beta film was formed at a jetting frequency of 2 Hz and an inter-dot pitch of 20 µm. After that, the beta film was dried at 70° C. for one hour, thereby forming an organic semiconductor film.

Organic thin-film transistor elements 5-2 to 5-8 (hereinafter, also referred to as "elements 5-2 to 5-8") were respectively produced according to the method for producing the element 5-1 except for the fact that the compositions for an organic thin-film transistor 22 to 28 were used instead of the composition for an organic thin-film transistor 21. The obtained elements 5-1 to 5-8 were considered as organic thin-film transistors of Examples 5-1 to 5-8.

—Flexo Printing Method—

An application liquid was prepared by dissolving the compound 1 (0.5% by mass), poly α-methylstyrene (0.5% by mass), and BYK323 (manufactured by BYK) (0.05% by mass) as a surfactant in tetralin and was used as a composition for an organic thin-film transistor 31. In addition, compositions for an organic thin-film transistor 32 to 36 were prepared in the same manner except for the fact that the respective compounds 2 and 5 to 8 were used instead of the compound 1.

An organic semiconductor film was formed on the same bottom gate-bottom contact-type substrate for measuring FET characteristics as in Example 2-1 using the composition for an organic thin-film transistor 31 and a flexo printing method, thereby obtaining a non-luminous organic thin-film transistor element 5-9 (hereinafter, also referred to as "element 5-9").

Meanwhile, the specific method for producing the organic semiconductor film using the flexo printing method is as described below.

As a printing apparatus, a flexo suitability tester F1 (manufactured by IGT Testing Systems K.K.) was used, and, as a flexo resin plate, an AFP DSH 1.70% (manufactured by Asahi Kasei Corporation)/a solid image was used. Printing was carried out at a pressure between the plate and the substrate of 60 N and a transportation rate of 0.4 m/second, and then the printed film was dried at 60° C. for two hours, thereby producing an organic semiconductor film (film thickness: 50 nm).

Organic thin-film transistor elements 5-10 to 5-14 (hereinafter, also referred to as "elements 5-10 to 5-14") were respectively produced according to the method for producing the element 5-9 except for the fact that the compositions for an organic thin-film transistor 32 to 36 were used instead of the composition for an organic thin-film transistor 31. The obtained elements 5-9 to 5-14 were considered as organic thin-film transistors of Examples 5-9 to 5-14.

<Evaluation>

The FET characteristics of each of the organic thin-film transistor elements (the elements 5-1 to 5-14) were evaluated using the same method as in Example 1-1. The results are shown in the following table.

TABLE 6

|  | Element No. | Material for organic thin-film transistor | Carrier mobility ($cm^2/Vs$) |
| --- | --- | --- | --- |
| Example 5-1 | Element 5-1 | Compound 1 | AA |
| Example 5-2 | Element 5-2 | Compound 2 | AA |
| Example 5-3 | Element 5-3 | Compound 3 | AA |
| Example 5-4 | Element 5-4 | Compound 4 | AA |
| Example 5-5 | Element 5-5 | Compound 5 | A |
| Example 5-6 | Element 5-6 | Compound 6 | A |
| Example 5-7 | Element 5-7 | Compound 7 | AA |
| Example 5-8 | Element 5-8 | Compound 8 | A |
| Example 5-9 | Element 5-9 | Compound 1 | A |
| Example 5-10 | Element 5-10 | Compound 2 | A |
| Example 5-11 | Element 5-11 | Compound 5 | A |
| Example 5-12 | Element 5-12 | Compound 6 | A |
| Example 5-13 | Element 5-13 | Compound 7 | A |
| Example 5-14 | Element 5-14 | Compound 8 | A |

From Table 6, it was confirmed that, in all of the organic thin-film transistor elements of the respective examples including the organic semiconductor layers obtained by forming a film of the compound represented by General Formula (1) of the present invention using the ink jet method or the flexo printing method, the carrier mobility was high. From this result, it is found that the compound represented by General Formula (1) of the present invention can be preferably used as organic thin-film transistor materials.

Examples 6-1 to 6-8

<Production of Inverter>

Figure 6:
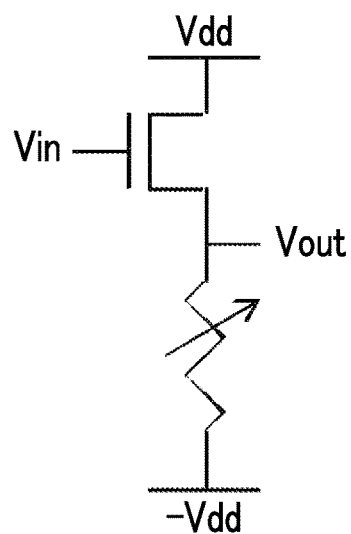
FIG. 6 is a schematic view of an inverter produced in the examples.

A variable resistance was connected to the organic thin-film transistor element of Example 1-1 as illustrated in FIG. 6, and the resistance value of the variable resistance was set to an appropriate value, thereby producing an inverter element 6-1. In addition, inverter elements 6-2 to 6-8 were produced using the organic thin-film transistor elements of Example 1-2 to Example 1-8 instead of the organic thin-film transistor element of Example 1-1. All of the inverter elements exhibited favorable inverter characteristics of 10 or higher gains.

Examples 7-1 to 7-8

<Production of Ring Oscillator>

Figure 7:
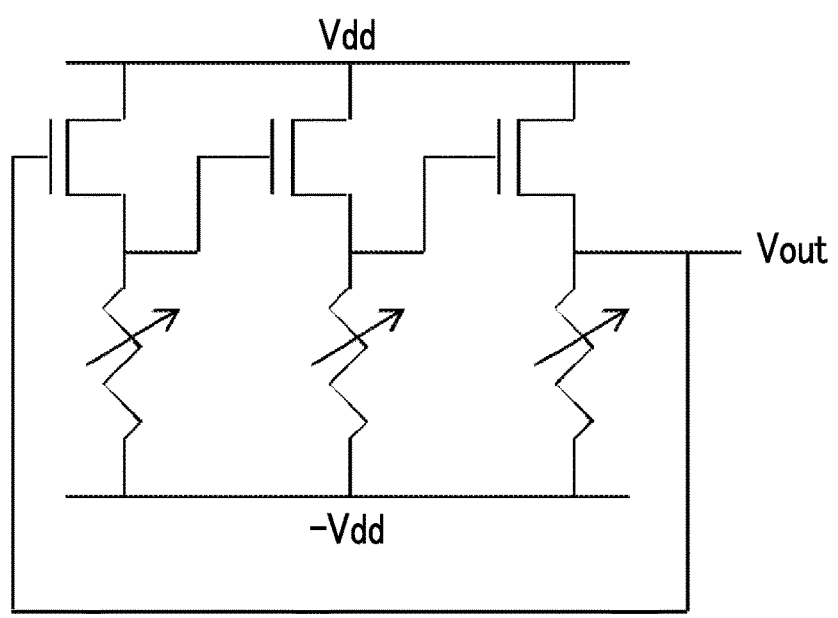
FIG. 7 is a schematic view of a ring oscillator produced in the examples.

The inverter elements of Example 6-1 were linked in three levels as illustrated in FIG. 7, thereby producing a ring oscillator element 7-1. In addition, ring oscillator elements 7-2 to 7-8 were produced using the inverter elements of Example 6-2 to Example 6-8 instead of the ring oscillator element of Example 6-1. All of the ring oscillator elements stably generated oscillations.

As described above, it has been shown that a variety of kinds of devices can be produced using the compound of the present invention.

EXPLANATION OF REFERENCES

10: substrate, 20: gate electrode, 30: gate insulating film, 40: source electrode, 42: drain electrode, 50: organic semiconductor layer (organic semiconductor film), 60: sealing layer, 100, 200: organic thin-film transistor. 210: composition for organic thin-film transistor, 212: substrate, 214: member, 216: pipette

What is claimed is:

1. An organic thin-film transistor comprising:
an organic semiconductor film including a compound which is represented by General Formula (1) and has a molecular weight of 3,000 or less, General Formula (1)

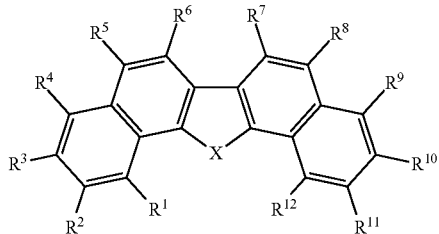

in General Formula (1), X represents an oxygen atom, a selenium atom, or a tellurium atom, $R^1$ to $R^{12}$ each independently represent a group represented by Formula (W), here, among $R^1$ to $R^{12}$, at least one group is a group other than a hydrogen atom, $$-L^W-R^W \qquad (W)$$

in Formula (W), $L^W$ is a divalent linking group of any of a single bond, —O—, —S—, —NR$^{13}$—, —CO—, —SO—, —SO$_2$—, or —Si(R$^{14}$)(R$^{15}$) or a divalent linking group obtained by bonding two or more divalent linking groups described above, $R^W$ represents a hydrogen atom or an alkyl group, an alkenyl group, an alkynyl group, an aryl group, or a heteroaryl group, all of which may have a substituent, and $R^{13}$ to $R^{15}$ each independently represent a hydrogen atom or an alkyl group, an alkenyl group, an alkynyl group, an aryl group, or a heteroaryl group, all of which may have a substituent, wherein, in General Formula (1), the number of carbon atoms included in each of $R^3$ and $R^{10}$ is independently 1 to 30.

2. The organic thin-film transistor according to claim 1, wherein, in General Formula (1), $R^3$ and $R^{10}$ each independently have, as $R^W$, an alkyl group having 1 to 20 carbon atoms, an alkynyl group having 2 to 6 carbon atoms, an aryl group having 6 to 20 carbon atoms, and a heteroaryl group having 3 to 20 carbon atoms, all of which may have a substituent.

3. The organic thin-film transistor according to claim 1, wherein, in General Formula (1), $R^1$ and $R^{12}$ are the same group, $R^2$ and $R^{11}$ are the same group, $R^3$ and $R^{10}$ are the same group, $R^4$ and $R^9$ are the same group, $R^5$ and $R^8$ are the same group, and $R^6$ and $R^7$ are the same group.

4. The organic thin-film transistor according to claim 1, wherein X is a selenium atom.

5. The organic thin-film transistor according to claim 1, wherein the compound is represented by General Formula (2), General Formula (2)

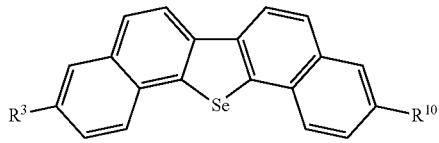

$R^3$ to $R^{10}$ are the same group and each represent a group represented by Formula (W), $$-L^W-R^W \qquad (W)$$

in Formula (W), $L^W$ is a divalent linking group of any of a single bond, —O—, —S—, —NR$^{13}$—, —CO—, —SO—, —SO$_2$—, or —Si(R$^{14}$)(R$^{15}$) or a divalent linking group obtained by bonding two or more divalent linking groups described above, $R^W$ represents an alkyl group having 1 to 20 carbon atoms, an aryl group having 6 to 20 carbon atoms, or a heteroaryl group having 3 to 20 carbon atoms, all of which may have a substituent, and $R^{13}$ to $R^{15}$ each independently represent a hydrogen atom or an alkyl group, an alkenyl group, an alkynyl group, an aryl group, or a heteroaryl group, all of which may have a substituent.

6. The organic thin-film transistor according to claim 5, wherein, in General Formula (2), $L^W$ is a single bond.

7. The organic thin-film transistor according to claim 1, wherein $R^3$ and $R^{10}$ each independently include a linear alkyl group.

8. A compound which is represented by General Formula (1) and has a molecular weight of 3,000 or less, General Formula (1)

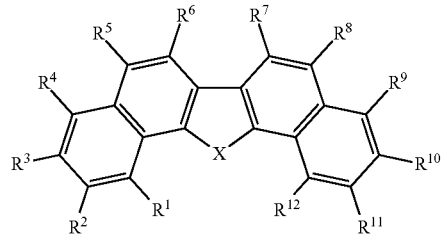

in General Formula (1), X represents an oxygen atom, a selenium atom, or a tellurium atom, $R^1$ to $R^{12}$ each independently represent a group represented by Formula (W), here, among $R^1$ to $R^{12}$, at least one group is a group other than a hydrogen atom, $$-L^W-R^W \qquad (W)$$

in Formula (W), $L^W$ is a divalent linking group of any of a single bond, —O—, —S—, —NR$^{13}$—, —CO—, —SO—, —SO$_2$—, or —Si(R$^{14}$)(R$^{15}$) or a divalent linking group obtained by bonding two or more divalent linking groups described above, $R^W$ represents a hydrogen atom or an alkyl group, an alkenyl group, an alkynyl group, an aryl group, or a heteroaryl group, all of which may have a substituent, and $R^{13}$ to $R^{15}$ each independently represent a hydrogen atom or an alkyl group, an alkenyl group, an alkynyl group, an aryl group, or a heteroaryl group, all of which may have a substituent, wherein, in General Formula (1), the number of carbon atoms included in each of $R^3$ and $R^{10}$ is independently 1 to 30.

9. The compound according to claim 8, wherein, in General Formula (1), $R^3$ and $R^{10}$ each independently have, as $R^W$, an alkyl group having 1 to 20 carbon atoms, an alkynyl group having 2 to 6 carbon atoms, an aryl group having 6 to 20 carbon atoms, and a heteroaryl group having 3 to 20 carbon atoms, all of which may have a substituent.

10. The compound according to claim 8,
wherein, in General Formula (1), $R^1$ and $R^{12}$ are the same group, $R^2$ and $R^{11}$ are the same group, $R^3$ and $R^{10}$ are the same group, $R^4$ and $R^9$ are the same group, $R^5$ and $R^8$ are the same group, and $R^6$ and $R^7$ are the same group.

11. The compound according to claim 8,
wherein X is a selenium atom.

12. The compound according to claim 8,
wherein the compound is represented by General Formula (2), General Formula (2)

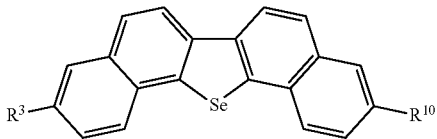

in General Formulae (2), $R^3$ to $R^{10}$ are the same group and each represent a group represented by Formula (W), $-L^W-R^W$ (W)

in Formula (W), $L^W$ is a divalent linking group of any of a single bond, —O—, —S—, —NR$^{13}$—, —CO—, —SO—, —SO$_2$—, or —Si(R$^{14}$)(R$^{15}$) or a divalent linking group obtained by bonding two or more divalent linking groups described above, $R^W$ represents an alkyl group having 1 to 20 carbon atoms, an aryl group having 6 to 20 carbon atoms, or a heteroaryl group having 3 to 20 carbon atoms, all of which may have a substituent, and
$R^{13}$ to $R^{15}$ each independently represent a hydrogen atom or an alkyl group, an alkenyl group, an alkynyl group, an aryl group, or a heteroaryl group, all of which may have a substituent.

13. The compound according to claim 12,
wherein, in General Formula (2), $L^W$ is a single bond.

14. The compound according to claim 8,
wherein $R^3$ and $R^{10}$ each independently include a linear alkyl group.

15. A material for an organic thin-film transistor comprising:
the compound according to claim 8.

16. A composition for an organic thin-film transistor comprising:
the compound according to claim 8; and
a solvent.

17. A method for manufacturing an organic thin-film transistor comprising:
a step of forming an organic semiconductor film by applying the composition for an organic thin-film transistor according to claim 16 on a substrate and drying the composition.

18. An organic semiconductor film comprising:
the compound according to claim 8.

* * * * *